(12) United States Patent
Foon et al.

(10) Patent No.: US 6,355,244 B1
(45) Date of Patent: Mar. 12, 2002

(54) METHODS AND COMPOSITIONS FOR THE TREATMENT OF PSORIASIS

(75) Inventors: Kenneth A. Foon; Malaya Chatterjee, both of Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/192,838

(22) Filed: Nov. 16, 1998

Related U.S. Application Data

(60) Provisional application No. 60/065,774, filed on Nov. 17, 1997.

(51) Int. Cl.$^7$ ............................................. A61K 39/395
(52) U.S. Cl. ............................... 424/131.1; 424/152.1; 530/387.2; 530/388.2
(58) Field of Search .......................... 424/131.1, 152.1; 530/387.2, 388.2

(56) References Cited

U.S. PATENT DOCUMENTS

| | | |
|---|---|---|
| 4,436,728 A | 3/1984 | Ribi et al. |
| 4,726,947 A | 2/1988 | Shimada et al. |
| 4,985,434 A | 1/1991 | Secrist, III et al. |
| 5,008,265 A | 4/1991 | Secrist, III et al. |
| 5,008,270 A | 4/1991 | Secrist, III et al. |
| 5,053,224 A | 10/1991 | Koprowski et al. |
| 5,057,540 A | 10/1991 | Kensil et al. |
| 5,077,284 A | 12/1991 | Loria et al. |
| 5,102,663 A | 4/1992 | Livington et al. |
| 5,141,742 A | 8/1992 | Brown et al. |
| 5,171,568 A | 12/1992 | Burke et al. |
| 5,308,614 A | 5/1994 | Hakomori |
| 5,330,977 A | 7/1994 | Tubaro et al. |
| 5,407,684 A | 4/1995 | Loria et al. |
| 5,500,215 A | 3/1996 | Hakomori |
| 5,529,922 A | 6/1996 | Chapman et al. |
| 5,571,900 A | 11/1996 | Wiegand et al. |
| 5,612,030 A | 3/1997 | Chatterjee et al. |
| 5,653,977 A | 8/1997 | Saleh |

FOREIGN PATENT DOCUMENTS

| | | |
|---|---|---|
| BE | 1008391 | 5/1996 |
| EP | 0 368 131 B1 | 5/1990 |
| EP | 0 443 518 A2 A3 | 8/1991 |
| EP | 0 661 061 A2 A3 | 7/1995 |
| JP | 6 145069 | 5/1994 |
| WO | WO 90/02809 | 3/1990 |
| WO | WO 90/10631 | 9/1990 |
| WO | WO 91/09603 | 7/1991 |
| WO | WO 91/11718 | 8/1991 |
| WO | WO 91/16924 | 11/1991 |
| WO | WO 92/01047 | 1/1992 |
| WO | WO 92/16231 | 10/1992 |
| WO | WO 92/19266 | 11/1992 |
| WO | WO 93/10134 | 5/1993 |
| WO | WO 93/21187 | 10/1993 |
| WO | WO 94/13804 | 6/1994 |
| WO | WO 94/16731 | 8/1994 |
| WO | WO 95/01355 | 1/1995 |
| WO | WO 95/04548 | 2/1995 |
| WO | WO 95/26718 | 10/1995 |
| WO | WO 96/20219 | 7/1996 |
| WO | WO 96/20277 | 7/1996 |
| WO | WO 96/22373 | 7/1996 |
| WO | WO 97/22694 | 6/1997 |

OTHER PUBLICATIONS

The Merck Index of Diagnosis and Therapy, vol. 17, chapter 117, 1999.*
*Animal Cell Culture: A Practical Approach*, R.I. Freshney, ed., IRL Press, 1987 (Table of Contents).
*Antibodies: A Laboratory Manual* Ed Harlow, David Lane, eds., Cold Spring Harbor Laboratory, New York, 1988 (Table of Contents).
Beardsley, Tim, "Crabshot [sic]. Manufactures gamble on cancer vaccines—again" *Scientific American* p. 102, Sep., 1994.
Bhattacharya–Chatterjee et al., "Idiotype vaccines against human T cell acute lymphoblastic leukemia. I. Generation and characterization of biologically active monoclonal anti-idiotypes" *J. Immunol.* 139:1354–1360, 1987.
*Bioworld Today*, pp. 001–006, Sep. 29, 1997.
Bird et al., "Single–chain antigen–binding proteins" *Science* 242:423–426, 1988.
"Cell Culture" *Methods in Enzymology*, vol. LVIII, William B. Jacoby, Ira H. Pastan, eds., Academic Press, 1979 (Table of Contents).
Chattopadhyay et al., "Murine monoclonal anti–idiotype antibody breaks unresponsiveness and induces a specific antibody response to human melanoma–associated proteoglycan antigen in cynomoglus monkeys" *Proc. Natl. Acad. Sci. USA* 89:2684–2688, 1992.
Cheresh et al., "Biosynthesis and expression of the disialoganglioside $G_{D2}$, a relevant target antigen on small cell lung carcinoma for monoclonal antibody–mediated cytolysis" *Cancer Res.* 46:5112–5118, 1996.
Cheung et al., "Ganglioside $G_{D2}$ specific monoclonal antibody 3F8. A Phase I study in patients with neuroblastoma and malignant melanoma" *J. Clin. Oncol.* 5:1430–1440, 1987.

(List continued on next page.)

*Primary Examiner*—Patrick J. Nolan
(74) *Attorney, Agent, or Firm*—Morrison & Foerster LLP

(57) ABSTRACT

This invention provides methods of treating psoriasis which entail eliciting an immune response in an individual against an antigen aberrantly expressed in psoriatic tissue, such as a ganglioside, in an individual. The anti-ganglioside immune response is elicited by administration of an antigen such as a ganglioside, an anti-idiotype moiety for a ganglioside, or a polynucleotide encoding an anti-idiotype moiety. Also described is a strategy for developing additional compositions for psoriasis. The compositions elicit an immunological response against a target antigen present on psoriatic tissue, which in turn can be detected using antibody affinity-purified from the serum of the treated subject. The presence of the immunological response correlates positively with control or resolution of the psoriatic symptoms.

4 Claims, 3 Drawing Sheets

OTHER PUBLICATIONS

Cheung et al., "Disialoganglioside $G_{D2}$ anti–idiotypic monoclonal antibodies" *Int. J. Cancer* 54:499–505, 1993.

Conry et al., "A carcinoembryonic antigen polynucleotide vaccine for human clinical use" *Cancer Gene Ther.* 2:33–38, 1995.

*Current Protocols in Immunology*, vol. 1, Supplement 28, John E. Coligan et al., eds., John Wiley & Sons, Inc., 1998 (Table of Contents).

*Current Protocols in Molecular Biology*, vol. 1, Supplement 30, 39, 40, Frederick M. Ausubel et al., eds., John Wiley & Sons, Inc., 1995 (Table of Contents).

Dabelsteen et al., "Cell surface glycosylation patterns in psoriasis" *APMIS* 98:221–228, 1990.

Denton et al., "Clinical outcome of colorectal cancer patients treated with human monoclonal anti–idiotypic antibody" *Int. J. Cancer* 57:10–14, 1994.

Fiedler et al., "High–level production and long–term storage of engineered antibodies in transgenic tobacco seeds" *Biotechnology* 13:1090–1093, 1995.

"Gene transfer vectors for mammalian cells" *Current Communications in Molecular Biology*, Jeffrey H. Miller, Michele P. Calos, eds., Cold Spring Harbor Laboratory, 1987 (Table of Contents).

Hamilton et al., "Ganglioside expression on human malignant melanoma assessed by quantitative immune thin–layer chromatography" *Int. J. Cancer* 53:566–573, 1993.

Hastings et al., "Production and characterization of a murine/human chimeric anti–idiotype antibody that mimics ganglioside" *Cancer Res.* 52:1681–1686, 1992.

Hawkins et al., "A genetic approach to idiotypic vaccination" *J. Immunother.* 14:273–278, 1993.

Heidenheim et al., "CDw60, which identifies the acetylated form of $G_{D3}$ gangliosides, is strongly expressed in human basal cell carcinoma" *Br. J. Dermatol.* 133:392–397, 1995.

Helling et al., "Ganglioside conjugate vaccines. Immunotherapy against tumors of neuroectodermal origin" *Mol. & Chem. Neuropath.* 21:299–309, 1994.

Herlyn et al., "Cloned antigens and antiidiotypes" *Hybridoma* 14:159–166, 1995.

"Immunochemistry and molecular immunology" *Weir's Handbook of Experimental Immunology* vol. 1, Donald M. Weir, Caroline Blackwell, eds., 1996 (Table of Contents).

Kanda et al., "Both $V_H$ and $V_L$ regions contribute to the antigenicity of anti–idiotypic antibody that mimics melanoma associated ganglioside $GM_3$" *Cell Biophysics* vol. 24,25:64–74, 1994.

Liang et al., "Differential display of eukaryotic messenger RNA by means of the polymerase chain reaction" *Science* 257:967–971, 1992.

Liang et al., "Recent advances in differential display" *Curr. Opin. Immunol.* 7:274–280, 1995.

Livingston, Philip O., "Construction of cancer vaccines with carbohydrate and protein (peptide) tumor antigens" *Curr. Opin. Immunol.* 4:624–629, 1992.

Livingston et al., "GD3/proteosome vaccines induce consistent IgM antibodies against the ganglioside GD3" *Vaccines* 11:1199–1204, 1993.

Livingston, Philip O., "Approaches to augmenting the immunogenicity of melanoma gangliosides: From whole melanoma cells to ganglioside–KLH conjugate vaccines" *Immunol. Review* 145:147–166, 1995.

Mackett et al., "The construction and characterisation of vaccinia virus recombinants expressing foreign genes" *DNA Cloning, vol. 11: A Practical Approach* Chapter 7, pp. 191–211.

Marks et al., "Phage libraries—a new route to clinically useful antibodies" *New Engl. J. Med.* 335:730–733, 1996.

McGuinness et al., "Phage diabody repertoires for selection of large numbers of bispecific antibody fragments" *Nature Biotechnol.* 14:1149–1154, 1996.

Mittelman et al., "Human high molecular weight melanoma–associated antigen (HMW–MAA) mimicry by mouse anti–idiotypic monoclonal antibody MK2–23: Induction of humoral anti–HMW–MAA immunity and prolongation of survival in patients with stage IV melanoma" *Proc. Natl. Acad. Sci. USA* 89:466–470, 1992.

Mittelman et al., "Kinetics of the immune response and regression of metastatic lesions following development of humoral anti–high molecular weight–melanoma associated antigen immunity in three patients with advanced malignant melanoma immunized with mouse antiidiotypic monoclonal antibody MK2–23" *Cancer Res.* 54:415–421, 1994.

*Molecular Cloning: A Laboratory Manual*, Second Edition, J. Sambrook et al., eds., Cold Spring Harbor Laboratory Press, 1989 (Table of Contents).

Moss, Bernard, "Vaccina virus: A tool for research and vaccine development" *Science* 252:1662–1667, 1991.

O'Boyle et al., "Immunization of colorectal cancer patients with modified ovine submaxillary gland mucin and adjuvants induces IgM and IgG antibodies to sialylated Tn" *Cancer Res.* 52:5663–5667, 1992.

Offner et al., "Lymphocyte stimulation by gangliosides, cerebrosides and basic protein in juvenile rheumatoid arthritis" *J. Clin. Lab. Immunol.* 6:35–37, 1981.

*Oligonucleotide Synthesis. A Practical Approach*, M.J. Gait, ed., IRL Press 1984 (Table of Contents).

Paller et al., "Absence of a stratum corneum antigen in disorders of epidermal cell proliferation: Detection with an anti–ganglioside $G_{M3}$ antibody" *J. Invest. Dermatol.* 92:240–246, 1989.

Paller et al., "Ganglioside $G_{M3}$ inhibits the proliferation of cultured keratinocytes" *J. Invest. Dermatol.* 100:841–845, 1993.

Pardoll, Drew, "New strategies for active immunotherapy with genetically engineered tumor cells" *Curr. Opin. Immunol.* 4:619–623, 1992.

Progenics Pharmaceuticals, Inc. Prospectus for sale of 2,000,000 shares of Common Stock subject to completion, dated Oct. 30, 1996.

*Remington's Pharmaceutical Sciences*, 18th Edition, Alfonso R. Gennaro, ed., Mack Publishing Co., PA, 1990 (Table of Contents).

Saleh et al., "Generation of a human anti–idiotypic antibody that mimics the GD2 antigen" *J. Immunol.* 151:3390–3398, 1993.

Samonigg et al., "Immune response to tumor antigens in a patient with colorectal cancer after immunization with anti-idiotypic antibody" *Clin. Immunol. Immunopathol.* 65:271–277, 1992.

Skov et al., "Lesional psoratic T cells contain the capacity to induce a T cell activation molecule CDw60 on normal keratinocytes" *Am. J. Pathol.* 150:675–683, 1997.

Sunday, Mary E., "Differential display RT–PCR for identifying novel gene expression in the lung" *Am. J. Physiol.* 269:L273–L284, 1995.

Takahashi et al., "Induction of CD8+ cytotoxic T cells by immunization with purified HIV–1 envelope protein in ISCOMs" *Nature* 344:873–875, 1990.

Tang et al., "Genetic immunization is a simple method for eliciting an immune response" *Nature* 356:152–154, 1992.

*The Polymerase Chain Reaction*, Kary B. Mullis et al., eds., Birkhäuser, 1994 (Table of Contents).

Yamamoto et al., "Anti–idiotype monoclonal antibody carrying the internal image of ganglioside GM3" *J. Natl. Cancer Inst.* 82:1757–1760, 1990.

* cited by examiner

Figure 2

```
      M    K    L    P    V    R    L    L    V    L    M    F    W    I    P    A
     ATG  AAG  TTG  CCT  GTT  AGG  CTG  TTG  GTG  CTG  ATG  TTC  TGG  ATT  CCT  GCT
      S    S    D
     TCC  AGC  GAT   (-1 to -19, leader)

D    V    L    M    T    Q    T    P    L    S    L    P    V    S    L    G
     GAT  GTT  TTG  ATG  ACC  CAA  ACT  CCA  CTC  TCC  CTG  CCT  GTC  AGT  CTT  GGA
      D    Q    A    S    I    S    C
     GAT  CAA  GCC  TCC  ATC  TCT  TGC    (1-23, Frame work 1)

R    S    S    Q    S    I    V    H    S    N    G    N    T    Y    L    E
     AGA  TCT  AGT  CAG  AGC  ATT  GTA  CAT  AGT  AAT  GGA  AAC  ACC  TAT  TTA  GAA
     (24-39, CDR 1)

W    Y    L    Q    K    P    G    Q    S    P    N    L    L    I    Y
     TGG  TAC  CTA  CAG  AAA  CCA  GGC  CAG  TCT  CCA  AAC  CTC  CTG  ATC  TAC
     (40-54, Frame work 2)

F    V    S    N    R    F    S
     TTT  GTT  TCC  AAC  CGA  TTT  TCT   (55-61, CDR 2)

G    V    P    D    R    F    S    G    S    G    S    G    T    D    F    T
     GGG  GTC  CCA  GAC  AGG  TTC  AGT  GGC  AGT  GGA  TCA  GGG  ACA  GAT  TTC  ACA
      L    K    I    S    R    V    E    A    E    D    L    G    V    Y    Y    C
     CTC  AAG  ATC  AGC  AGA  GTG  GAG  GCT  GAG  GAT  CTG  GGA  GTT  TAT  TAC  TGC
     (62-93, Frame work 3)

F    Q    G    S    H    V    P    W    T
     TTT  CAA  GGT  TCA  CAT  GTT  CCG  TGG  ACG
     (94-102, CDR 3)

F    G    G    G    T    K    L    E    I    K
     TTC  GGT  GGA  GGC  ACC  AAG  CTG  GAA  ATC  AAA
     (103-112, Frame work 4)

R    A    D    A    A    P    T    V    S    I    F    P    P
     CGG  GCT  GAT  GCT  GCA  CCA  ACT  GTA  TCC  ATC  TTC  CCA  CCA

S    S    K    L    G
     TCC  AGT  AAG  CTT  GGG    (Constant region)
```

Figure 3

```
  M    A    V    L    G    L    L    F    C    L    V    T    F    P    S    C
 ATG  GCT  GTC  TTG  GGG  CTG  CTC  TTC  TGC  CTG  GTG  ACA  TTC  CCA  AGC  TGT
  V    L    S
 GTC  CTG  TCC    (-1 to -19, Leader)

Q    V    Q    V    K    E    S    G    P    F    L    V    P    P    S    Q
 CAG  GTG  CAG  GTG  AAG  GAG  TCA  GGA  CCT  TTC  CTG  GTG  CCC  CCC  TCA  CAG
  S    L    S    I    T    C    T    V    S    G    F    S    L    T
 AGC  CTG  TCC  ATC  ACA  TGC  ACT  GTC  TCA  GGG  TTC  TCA  TTA  ACC
 (1-30, Frame work 1)

T    Y    G    V    S
 ACC  TAT  GGT  GTA  AGC    (31-35, CDR 1)

W    I    R    Q    P    P    G    K    G    L    E    W    L    G
 TGG  ATT  CGC  CAG  CCT  CCA  GGA  AAG  GGT  CTG  GAG  TGG  CTG  GGA
 (36-49, Frame work 2)

A    I    W    G    D    G    T    T    N    Y    H    S    A    L    I    S
 GCA  ATT  TGG  GGT  GAC  GGG  ACC  ACA  AAT  TAT  CAT  TCA  GCT  CTC  ATA  TCC
 (50-65, CDR 2)

R    L    S    I    S    K    D    N    S    K    S    Q    V    F    L    K
 AGA  CTG  AGC  ATC  AGC  AAG  GAT  AAC  TCC  AAG  AGC  CAA  GTT  TTC  TTA  AAA
  L    N    S    L    Q    T    D    D    T    A    T    Y    Y    C    A    K
 CTG  AAC  AGT  CTG  CAA  ACT  GAT  GAC  ACG  GCC  ACG  TAC  TAC  TGT  GCC  AAA
 (66-97, Frame work 3)

L    G    N    Y    D    A    L    D    Y
 CTG  GGT  AAC  TAC  GAT  GCT  CTG  GAC  TAC
 (98-106, CDR 3)

W    G    Q    G    T    S    V    T    V    S    S
 TGG  GGT  CAA  GGA  ACC  TCA  GTC  ACC  GTC  TCC  TCA
 ( 107-117, Frame work 4)

A    K    T    T    P    P    P    V    Y    P    L    V    P    G    S    L
 GCC  AAA  ACG  ACA  CCC  CCA  CCC  GTC  TAT  CCA  TTG  GTC  CCT  GGA  AGC  TTG  GG
 (Constant region)
```

METHODS AND COMPOSITIONS FOR THE TREATMENT OF PSORIASIS

REFERENCE TO RELATED APPLICATIONS

This application claims the priority benefit of U.S. Provisional Patent Application No. 60/065,774, filed Nov. 17, 1997. The priority application is hereby incorporated herein by reference in its entirety.

STATEMENT OF RIGHTS TO INVENTIONS MADE UNDER FEDERALLY SPONSORED RESEARCH

This invention was made in part during work supported by a grant from the United States Public Health Service (CA72018). The government has certain rights in the invention.

BACKGROUND

Psoriasis is a chronic condition that affects as much as 2.6% of the population of the developed world. A recent survey reported by the National Psoriasis Foundation estimates that 6.4 million people suffers from psoriasis, of which about 500,000 is rated as severe. The annual patient cost for treating psoriasis is currently estimated at $1.6 to $3.2 billion. Every year, about 400 people are granted disability by the Social Security Administration, and another 400 people die from psoriasis-related causes.

Characteristics of Psoriasis

It is not known what causes psoriasis, although there is evidence of a genetic predisposition and an autoimmune etiology. Onset may be triggered by systemic infections such as strep throat, skin injury, vaccinations, and certain oral medications such as steroids. Subsequently, the immune system is thought to induce inflammation and excessive skin cell reproduction, which can be exacerbated by additional factors such as stress and diet.

In normal skin, the time for a cell to move from the basal layer through the granular layer is 4–5 weeks. In psoriatic lesions, the time is decreased 7–10 fold because of a shortened cell cycle time, an increase in the absolute number of cells capable of proliferating, and an increased rate of division. T cell mediated immune responses appear to be responsible for the inflammation and hyperproliferation of keratinocytes. Neutrophils are found in psoriatic lesions, associated with increased levels of plasminogen activator. Psoriatic fibroblasts have increased levels of enzymes involved in collagen synthesis, secondary to expansion of the papillary dermis. Psoriatic plaques comprise HLA-DR positive keratinocytes and Langerhans cells, and activated T cells expressing elevated levels of IL-2 receptors.

The typical lesion of psoriasis is a well-demarcated erythematous plaque, covered by thick, silvery scales. Psoriasis can become so extensive as to cause exfoliative erythroderma, in which the entire epidermal surface is in a state of hyperproliferation. Gluttate psoriasis is a form of the disease following streptococcal pharyngitis, with widely distributed characteristic 1–3 cm lesions. Pustular psoriasis is characterized by numerous sterile pustules of 2–5 mm in diameter, and may lead to an acute, explosive, life-threatening episode of fever, chills, leukocytosis, hypoalbuminemia, and hypocalcemia, demanding immediate, vigorous therapy. Previously stable plaque-type psoriasis can be acutely exacerbated by viral infections, particularly HIV. Psoriasis is also associated with five different forms of psoriatic arthritis, including distal interpharangeal involvement; an asymmetric, oligoarticular pattern; a symmetric polyarthritis; arthritis mutilans; and sacroiliitis and spondylitis.

The inflammation and hyperproliferation of psoriatic tissue is associated with a different histological and antigenic profile than normal skin. Dabelsteen et al. used a panel of anti-carbohydrate monoclonal antibodies to compare psoriatic tissue with the surrounding dermis. The glycosylation pattern in psoriatic epithelium is changed in two ways: some carbohydrates are expressed at an earlier stage of cell maturation. In addition, certain biosynthetic precursor antigens not expressed in normal skin were found in psoriatic skin.

Paller et al. (1989) investigated the distribution of ganglioside GM3 using an antibody designated 8G9D8. At the electron microscope level, antibody deposition was seen in the corneocyte envelope. Disposition was significantly decreased or absent in disorders of excessive keratinocyte proliferation, including squamous cell carcinomas, congenital ichthysiform erythrodermas, prokeratosis, and psoriasis. In a subsequent study, Paller et al. (1993) found that when GM3 was added to keratinocytes from normal foreskin, lesional skin from patients with psoriasis or ichthyosis, and to cutaneous squamous carcinoma lines, it inhibited growth in a dose-dependent manner at concentrations of 10–100 $\mu M$. Confluent undifferentiated keratinocytes were least sensitive. The gangliosides GD3, 9-O-acetyl-GD2, and GD1b also inhibited keratinocyte proliferation. Gangliosides GM1 and GD1a, and sialic acid had little effect. The authors concluded that preferential activation of sialyltransferase II may be involved in control of keratinocyte growth, but not differentiation.

Concharenko et al. studied ganglioside expression on the erythrocytes and serum of healthy subjects, and patients with psoriasis. During phases of exacerbation, a marked decrease was observed in the content of GM2 and GM3 fractions of the red cells, and GD1a decreased in serum. The presence of a new monosialoganglioside fraction was noted during exacerbation, both in serum and on red cells. The ganglioside spectrum of patients in clinical remission of psoriasis was almost normal.

Heidenheim et al. describe a monoclonal antibody designated UM4D4 which recognizes the cell surface marker CDw60. This marker is present on a subset of normal T cells, melanocytes, malignant melanoma cells, and hyperproliferative psoriatic keratinocytes. CDw60 antibodies bind to the acetylated form of GD3. 74% of basal cell carcinomas express CDw60, whereas CDw50 expression in normal skin is confined to melanocytes and a few scattered keratinocytes at the basal cell layer. Skov et al. recently reported that in psoriatic skin, basal and suprabasal keratinocytes express CDw60. Cloned T cell lines obtained from lesional skin upon initiation were found to release a cocktail of soluble factors including IL-4 and IL-13, that up-regulated CDw60 expression on cultured normal keratinocytes.

Currently Available Treatments for Psoriasis

Classical treatments of psoriasis include calciptriene (a vitamin $D_3$ derivative), topical coal tar preparations, systemic antimitotic agents such as methotrexate, and retinoids, particularly etretinate. Extensive psoriasis can be treated by photosensitization with oral 8-methoxypsoralen, followed by ultraviolet A. Corticosteroids are given for psoriatic arthritis and acute attacks of pustular psoriasis. More recently, cyclosporin A has been tested in clinical trials at doses of 3–7 mg/kg with promising results, but associated with the risk of renal toxicity. There is no cure.

Current biotechnology approaches to psoriasis treatment relate to a direct pharmaceutical-mediated attack, either on cell proliferation or on the immune component of the disease. Japanese patent application JP 6145069 describes angiogenesis inhibitors comprising ganglioside GM3 or a GM3 analog as an active agent. At 100 μg/mL, GM3 showed growth of normal human antioendothelial cells of $4.5 \times 10^4$ on day 5, compared with $76 \times 10^4$ in controls. U.S. Pat. No. 5,339,977 describes n-deacetyl-lysoganglioside derivatives for use as phospholipase A2 inhibitors for the treatment of proliferative and autoimmune diseases, including various forms of cancer, psoriasis, and rheumatoid arthritis.

An IL-2 fusion toxin has been developed (Seragen, Inc.) that is designed to selectively destroy activated T cells in psoriatic plaques, leaving normal cells alone. The objective is to destroy activated T cells, and thereby clear the psoriasis. A Phase II study has been performed in which test doses of 5, 10, and 15 μg/kg were administered per day. Comparable improvement was observed in patients with moderate to severe psoriasis. However, in order to obtain this response, the compound was administered three days per week for four weeks.

Various formulations containing the compound BCX-34 for psoriasis, cutaneous T cell lymphoma, and HIV infection have been tested (Bioworld Today, Sep. 29, 1997; see also WO 95/01355; WO 93/21187; WO 90/10631; U.S. Pat. Nos. 5,008,270, 5,008,265, and 4,985,434). BCX-34 is a small molecule drug that inhibits purine nucleoside phosphorylase, a human enzyme believed to be involved in the proliferation of T cells. An oral formulation is being tested in an ongoing Phase I/II trial. A topical formulation advanced to the Phase III stage for both lymphoma and psoriasis. The Phase III psoriasis study showed only a 14% greater improvement in mean lesion scores in the treated group compared to placebos, which for these studies was not statistically significant.

Accordingly, there is a need for therapeutic compositions that are effective in managing psoriasis, particularly if they are effective when given on an occasional basis. The present invention relates to a strategy in which the patient's own immune system is recruited into an active role against the disease.

SUMMARY OF THE INVENTION

The invention provides methods of using compositions which elicit an immune response against an antigen that is aberrantly expressed in psoriatic tissue.

Accordingly, in one aspect, the invention provides methods for treating psoriasis in an individual, comprising administering a composition effective in stimulating a specific immunological response against an antigen aberrantly expressed in human psoriatic tissue. These composition(s) comprise an antigen that shares immunological characteristics of an antigen that is aberrantly expressed in psoriatic tissue (such as human psoriatic tissue). Antigens aberrantly expressed in psoriasis include but are not limited to gangliosides. While a detectable immunological response is likely to be beneficial, efficacy can also be deduced by an improvement in symptoms or control of the psoriatic condition beyond what would be expected without treatment.

Certain embodiments of the invention include methods for treating psoriasis in an individual by eliciting an anti-ganglioside immunological response in the subject. The immunological response can be elicited using any suitable immunogen and/or immunogenic composition, such as: (1) a ganglioside in an immunogenic form, such as GM2, GM3, GD1b, GD2, 9-O-acetyl GD2, GD3, GD3 lactone, 9-O-acetyl GD3, and GT3; (2) an anti-idiotype for a ganglioside, such as the monoclonal antibodies 1A7, 4B5, or BEC-2; or (3) a polynucleotide encoding an anti-idiotype for a ganglioside. The immunological response can have humoral or cellular components, and preferably has both.

Further embodiments of the invention relate to preparing a composition for use in the treatment of psoriasis by preparing a composition comprising the determinant in an immunogenic form, or else raising an anti-idiotype against a monoclonal antibody that binds the antigenic determinant. Also embodied are methods for screening a composition for efficacy in treating psoriasis, involving administering the composition to human subjects, and monitoring disease progression (optionally in combination with immunological parameters) following treatment.

A further embodiment of the invention is a composition containing a ganglioside, an anti-idiotype for a ganglioside, or a polynucleotide encoding a ganglioside, packaged with an indication of its suitability for use in treating psoriasis.

Further embodiments of the invention relate to the use of a component selected from the group consisting of a ganglioside, an anti-idiotype for a ganglioside, and an expression vector encoding an anti-idiotype for a ganglioside, in the manufacture of a medicament for the treatment of psoriasis.

BRIEF DESCRIPTION OF THE FIGURES

FIG. 2 is a depiction of the cDNA sequence (SEQ ID NO:1) and the amino acid sequence (SEQ ID NO:2) of the light chain variable region of 1A7 and adjoining residues.

FIG. 3 is a depiction of the cDNA sequence (SEQ ID NO:3) and the amino acid sequence (SEQ ID NO:4) of the heavy chain variable region of 1A7 and adjoining residues.

DETAILED DESCRIPTION

Figure 1:
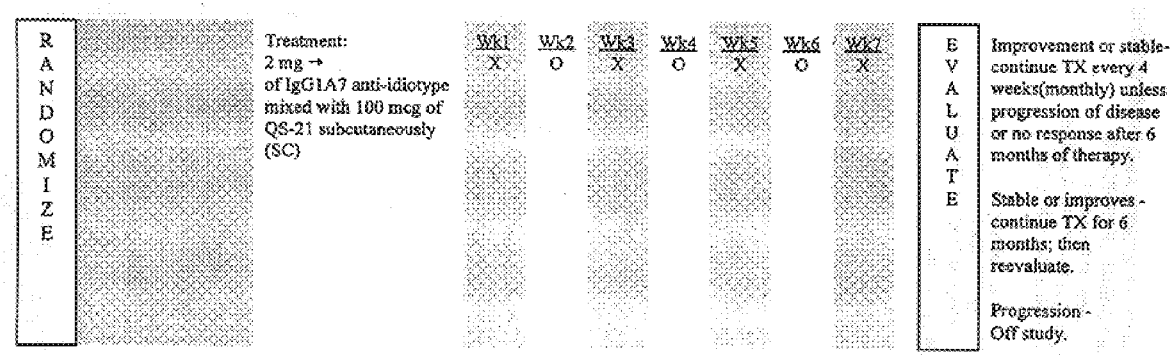
FIG. 1 is a scheme for evaluating the effect of raising an anti-GD2 immunological response using an anti-idiotype vaccine to treat individuals with severe chronic plaque psoriasis.

It is an object of this invention to provide compositions that are newly applied in the treatment of psoriasis in its various manifestations. Ideally, the compositions promote resolution of the clinical features, but stabilization of the condition is a satisfactory outcome. It is desirable that the effect be enduring, so that once an effect is achieved, readministration of the composition, if any, need occur on only an occasional basis. To accomplish this, the usual mode is to recruit active participation of the immune system of the host to react against a target antigen on psoriatic tissue.

This invention is based in part on the discovery that patients immunized systemically with a suitable vaccine composition mount a response directed against a psoriasis-specific antigen. As illustrated in Example 3, the response includes circulating antibodies that specifically adhere to affected tissue. Without intending to be bound by theory, it may be that the immune response to the target antigen promotes elimination or metabolic down-regulation of cells bearing the target antigen, or that it interferes mechanistically with a pathological phenotype of affected cells (such as proliferation) that is mediated, at least in part, by the target antigen. As a result, the presence of the immune response promotes the clinical resolution of the condition.

Several target antigens are believed to be suitable as vaccine targets in psoriasis, and various types of vaccines can be used to obtain the desired result. Illustrative examples are given in the sections that follow.

Definitions

In reference to the therapeutic methods and compositions of this invention, the term "psoriasis" refers to all skin conditions in the clinical arts described by this term, and to psoriatic-associated conditions, including psoriatic arthritis.

"Psoriatic tissue" refers to tissue affected by psoriasis and affected cells contained within the tissue, but not to cells that have migrated to the site such as leukocytes. Preferably, the psoriatic tissue is from a human.

Particular molecules referred to in this disclosure, such as CEA, gangliosides designated GM1, GM2, and so on, are meant to include not only the intact molecule, but also allotypic and synthetic variants, synthetic analogs, fusion molecules, conjugates, and other derivatives that contain the parent molecule and its fragments that are recognized by antibodies specific for the intact molecule.

An "effective amount" is an amount sufficient to effect a beneficial or desired clinical result. An effective amount can be administered in one or more doses. For purposes of this invention, an effective amount of ganglioside, antibody, or other composition is an amount that induces an immune response against a psoriasis antigen.

"Immunological activity" of a particular immunogen or vaccine component refers to the ability to raise an immune response. A specific immune response may comprise antibody, B cells, T cells, and any combination thereof, and effector functions resulting therefrom. Included are the antibody-mediated functions ADCC and complement-mediated cytolysis (CMC). A T cell response can include T helper cell function, cytotoxic T cell function, or inflammation/inducer T cell function. A compound or composition able to elicit a specific immune response according to any of these criteria is referred to as "immunogenic".

An antigen that "shares immunological characteristics" with another antigen is an antigen that, when administered in appropriate form (such as, for example, alone, in conjunction with an adjuvant, in association with (or conjugated to) a compound), elicits an immunological activity. For purposes of this invention, it is also understood that an antigen comprises an antigenic determinant(s) (as is well understood in the art).

A "polynucleotide" is a polymeric form of nucleotides of any length, which contain deoxyribonucleotides, ribonucleotides, and nucleotide analogs in any combination. A "vector" refers to a recombinant DNA or RNA plasmid or virus that comprises a heterologous polynucleotide to be delivered into a target cell, either in vitro or in vivo.

The terms "polypeptide", "peptide" and "protein" are used interchangeably to refer to polymers of amino acids of any length, and may be interrupted by non-amino acids.

An "aberrantly expressed antigen" is an antigen that is uniquely expressed, overexpressed, and/or underexpressed in conjunction with a disease state. For purposes of this invention, the disease state is psoriasis.

An "immunogenic form" of an antigen is a form of or formulation comprising the antigen which renders the antigen immunogenic. Such forms include, but are not limited to, antigen alone, antigen in conjunction with one or more adjuvants, antigen in association with or conjugated to a moiety, such as a hapten.

A "host cell" denotes a eukaryotic cell that has been genetically altered, or is capable of being genetically altered by administration of an exogenous polynucleotide, such as a recombinant plasmid or vector. When referring to genetically altered cells, the term refers both to the originally altered cell, and to its progeny.

An "isolated" polynucleotide, polypeptide, ganglioside, or other component, is one that is substantially free of the materials with which it is associated in nature. Substantially free means at least 50%, preferably at least 75%, more preferably at least 90%, and even more preferably at least 98% free of the materials with which it is associated in nature, other than solvent.

A "vaccine" is a pharmaceutical composition for human or animal use, which is administered with the intention of conferring the recipient with a degree of specific immunological reactivity against a particular target, or group of targets. The immunological reactivity may be desired for experimental purposes, for treatment of a particular condition, for the elimination of a particular substance, or for prophylaxis. An active vaccine is a vaccine intended to elicit an immune response in the recipient that persists in the absence of the vaccine components.

"Adjuvant" as used herein in the context of a pharmaceutical preparation is a chemical or biological agent given in combination with an antibody, polynucleotide or polypeptide to enhance its immunogenicity.

An "individual" or "subject" treated according to this invention is a vertebrate, preferably a mammal, more preferably a human. Mammals include, but are not limited to, farm animals, sport animals, rodents, primates, and pets.

Other terms used in this disclosure are explained where they arise.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991).

All patents, patent applications, articles and publications mentioned herein, both supra and infra, are hereby incorporated herein by reference.

Target Antigens in Psoriatic Tissue

The target antigen against which a specific immune response is desired contains an epitope or antigenic determinant which is aberrantly expressed in psoriatic tissue. This means that it is present in cells of the affected tissue (or the surrounding milieu) in a manner that makes it accessible to the immune system at a level that is significantly different than in cells of the same tissue type that are not affected. The cells in which the epitope is aberrantly expressed will be resident cells of the affected area, particularly keratinocytes or living epithelial cells, rather than migrant cells. For purposes of this invention, compositions described herein may comprise an antigen or an antigenic determinant.

The aberrantly expressed antigenic determinant of interest can be of any chemical nature, including but not limited to protein epitopes, carbohydrate epitopes, and glycolipids such as gangliosides. Typically, the epitope is uniquely expressed and/or overexpressed in psoriatic tissue in a variety of different individuals, although variations in expression level may occur. Typically, the determinant will be expressed at the cell surface or present as an insoluble but accessible antigenic mass, rather than being a soluble factor. Histocompatibility Class I or Class II antigens are excluded by definition.

Antigenic determinants that are aberrantly expressed can be identified by a number of techniques known in the art. One method is to look for a particular messenger RNA transcript that is present in an unusual abundance in affected cells. Where the determinant is a protein antigen synthesized by the cell, a suitable proxy is, for example, mRNA encoding the antigen. Where the determinant is a carbohydrate or glycolipid, a suitable proxy is, for example, mRNA encoding an enzyme involved in forming a critical antigen-specific linkage in the synthetic pathway.

Methods for determining mRNA that is in an unusual abundance in one cell than another involves preparing mRNA from both cells, and then comparing the amount of each particular mRNA between the preparations. A number of techniques for the comparison step are related in some way to subtractive hybridization. One example involves producing positive and negative cDNA, respectively, from the first and second RNA preparations, and looking for cDNA which is not completely hybridized by the opposing preparation. Subtractive hybridization is described in the standard molecular biology reference books listed earlier.

Another way of comparing production of particular messenger RNA is by differential display. This has been extensively described by Liang et al. (1992, 1995), and has since been elaborated in a number of different ways. In this technique, cDNA is prepared from only a subpopulation of each RNA preparation, and expanded via the polymerase chain reaction using primers of particular specificity. Similar subpopulations are compared across several RNA preparations for expression differences by gel autoradiography. In order to survey the RNA preparations entirely, the assay can be repeated with a comprehensive set of PCR primers. The screening strategy more effectively includes multiple positive and negative control samples (Sunday et al.). By excising the corresponding region of the separating gel, it is possible to recover and sequence the cDNA.

Antigenic determinants that are aberrantly expressed in psoriatic tissue can also be identified directly using antibodies directed against them. Psoriatic tissue or an antigen extract can be used to screen an immunoglobulin library. More conveniently, if the practitioner suspects a particular antigen of being aberrantly expressed in psoriatic tissue, an antibody specific to the antigen can be provided and used to test psoriatic tissue. Confirmation of the overexpression can be obtained, for example, by performing a standard immunoassay on solubilized tissue extract of affected tissue, and comparing with a similar extract of unaffected tissue. More preferable are immunohistology techniques, using the antibody specific for the suspected target as the primary antibody. A suitable aberrantly expressed determinant will result in different staining in a section from affected tissue than unaffected tissue, and will also show specificity for particular cells in the affected sample. An illustration of this is provided in Example 1.

Possible candidate antigens include any naturally occurring ganglioside antigens, antigens that are aberrantly expressed in a spectrum of different cancers, such as CEA, alpha-fetoprotein and gp-72, and antigens that are aberrantly expressed in cancers of the skin, especially but not limited to melanoma. Melanoma-associated antigens include the gangliosides GM2, GD2, GD3, and their derivatives and analogs; HMW-MAA, MPG, and gp-75. Also of interest are the Thomsen-Friedenreich (T) antigen (Galβ1-3GalNAcα-O-Ser), Tn, and sialylated Tn (New5Acα2-6GalNAcα-O-Ser). Also of interest is the cell surface marker CDw60.

Glycolipids suitable as target antigens include any of the monosialyl, disialyl and trisialyl gangliosides that occur naturally on cells in psoriatic tissue. Preferred target antigens are GM1, GD1a, GT1, GT2, and especially GM2, GM3, N-glycolyl GM3, GD1b, 9-O-acetyl GD2, GD3, GD3 lactone, 9-O-acetyl GD3, and GT3.

Types of Therapeutic Compositions used in this Invention

Once a suitable target antigen is identified, a composition is designed with a view to recruiting a specific immune response in the subject to be treated against the aberrantly expressed determinant. Any type of composition capable of eliciting the desired specific immune response is suitable.

In some embodiments, the invention employs a composition comprising the target antigen, or a modified version, in an immunogenic form. In other embodiments, an effective amount of a composition is employed, wherein an effective amount is an amount sufficient to elicit the desired immune response. Accordingly, the antigen is administered in a composition such that an immune response is elicited. For example, the target antigen can be provided by obtaining an enriched fraction from a suitable tissue source or cell line, such as keratinocytes, using one of the assays described earlier to follow the desired activity. An illustration of this is a vaccine for the Tn and sialylated Tn antigens, which can be prepared from ovine submaxillary gland mucin (O'Boyle et al.).

More typically, the target antigen is provided in synthetic form. Where the target antigen is not previously known, it is first characterized by isolation of the antigen complex, or an mRNA encoding it. Protein antigens can then be prepared by standard peptide synthesis, or by expressing a polynucleotide encoding it in a suitable host cell. Carbohydrate and other non-protein antigens are generally prepared by chemical synthesis, or by a combination of synthetic and isolation techniques. For example, use of cancer antigens as vaccine preparations is described in BE 1008391 and WO 92/19266 (CEA antigen), and in U.S. Pat. No. 5,141,742 (melanoma-associated antigen p97).

Also suitable for use in immunogenic compositions to raise an anti-ganglioside response are any monosialyl, disialyl and trisialyl gangliosides, along with synthetic derivatives, including 9-O-acetyl derivatives, lactone and lactam derivatives and analogs, and episialo derivatives; many of which are referred to elsewhere in this disclosure.

Included in the practice of the invention is the application to psoriasis of ganglioside vaccines and other formulations originally designed for cancer treatment or other modes of clinical care. For example, Helling et al. and Livingston et al. describe ganglioside GD3, in the form of synthetic multiple antigenic peptides, as conjugates with albumin, KLH, or membrane proteins of *Neiseeria meningitidis,* or as proteosomes. A vaccine for stimulating or enhancing production of antibodies against 9-O-acetyl GD3 is outlined in U.S. Pat. No. 5,102,663. European patent application EP 0443518 outlines a cancer vaccine containing episialo complex carbohydrates, particularly epiGM3, epiGM4, or epiGM5. European patent application EP 0661061 outlines vaccine compositions for eliciting an immune response against N-glycosylated gangliosides for cancer treatment, particularly N-glycolyl GM3. PCT patent application WO 93/10134 outlines ganglioside lactam analogue derivatives that are proposed for use in a vaccine for cancer treatment. Cheresh et al. describe the biosynthesis and expression of the disialoganglioside GD2, a relevant target antigen on small cell lung carcinoma for monoclonal antibody-mediated cytolysis. PCT patent application WO 94/16731 outlines ganglioside-KLH conjugate vaccines with the adjuvant QS-21, using a ganglioside selected from GM2, GM3, GD2, GD3, GD3 lactone, O-acetyl GD3, and GT3. The metabolism of these gangliosides is altered in cancers of neuroectodermal origin, including melanoma (Hamilton et al.). Progenics Pharmaceuticals Inc. is testing a GM2-KLH conjugate with the adjuvant QS-21 in a Phase III clinical trial of patients with melanoma under the product name GMK. Also being tested is a second ganglioside conjugate vaccine, MGV, comprising a combination of KLH-conjugated GD2 and GM2. The vaccine is proposed for therapy not only of melanoma, but also of colorectal cancer, lymphoma, small cell lung cancer, sarcoma, gastric cancer, and neuroblastoma (Progenics Prospectus). Any of these compositions or their active components may be adapted for psoriasis treatment in accordance with this invention.

Another illustration of a composition suitable for eliciting a specific immunological response against a target antigen in psoriasis is an anti-idiotype moiety. This approach to immunization arises from the network theory of Jerne, involving a second antibody (Ab2) raised against a first antibody (Ab1) which in turn is specific for the target. The Ab2 is selected not only for its ability to bind Ab1 specifically, but also for its ability to stimulate a further antibody (Ab3) that cross-reacts with the target. The use of anti-idiotypes in cancer treatment is described generally in U.S. Pat. No. 5,053,224.

The term "anti-idiotype" or "anti-idiotype moiety" as used throughout this application is defined to include not only intact antibody molecules, but any molecules comprising at least one variable region or portion of a variable region with the desired functional properties. The variable region will typically comprise a $V_H$–$V_L$ pair, but may alternatively be made up of other combinations of variable chains from antibodies or T cell receptors. Variable region fragments, fusion molecules, chimeras, and humanized variants are included, so long as the requisite functional properties are retained. The variable region may be presented in any suitable form, including but not limited to intact antibody molecules, antibody fragments (such as Fab, F(ab')$_2$, and Fv), multiple antigen proteins, and various antigen-binding constructs. Examples of constructs of particular interest include fusion constructs, such as single chain variable region polypeptides (scFv), in which a single $V_H$–$V_L$ pair are linked through a flexible peptide linker sequence in a manner that permits the polypeptide to fold into the three-dimensional conformation of a single variable region. Also included are diabodies, in which two variable regions are linked by a shorter linker that prevents folding into a single variable region, but permits chains to dimerize into bivalent molecules with two $V_H$–$V_L$ sites. Other constructs of interest include polymeric forms, which contain a plurality (i.e., more than one) polypeptide. Polymeric forms may be linear or branched.

The desirable characteristics of an anti-idiotype moiety are an ability to bind an antibody specific for the target antigen (Ab1), and the ability to elicit an antibody specific for the target antigen when injected into the intended subject. As used herein, reference to an anti-idiotype for a particular antigen (for example, an anti-idiotype for a ganglioside) means an anti-idiotype that elicits an active immune response specific for the particular antigen in an individual when administered in an immunogenic form.

To obtain an anti-idiotype with the features desired, a screening process is employed. A preferred screening method involves the following steps: (1) Positive selection for antibody (or at least a molecule having a variable region) capable of binding to the Ab1; (2) Negative selection against antibody recognizing isotypic or allotypic determinants of the Ab1; (3) Positive selection for an ability to inhibit the binding of Ab1 to the target antigen; and (4) Positive selection for an ability to induce a humoral immune response against the target antigen in experimental animals. Typically, the first step involves multiple immunization of an animal with the Ab1, preparation and cloning of hybridoma cells from the immune animal, and then testing of the cells for the desired specificity on a clone-by-clone basis. However, other ways of raising or selecting antibody or antibody equivalents are also suitable. Immunocompetent phage can be constructed to express immunoglobulin variable region segments on their surface. See Marks et al., New Engl. J. Med. 335:730, 1996; International patent applications WO 94/13804, WO 92/01047, and WO 90/02809; and McGuinness et al., Nature Biotechnol. 14:1149, 1996. Phage of the desired specificity can be selected, for example, by adherence to Ab1 attached to a solid phase, and then amplified in *E. coli*. A further elaboration of the screening method and its use in preparing an anti-idiotype for a ganglioside is provided in International Patent Application WO 96/22373.

Of particular interest are the monoclonal antibodies (and derivatives with the same immunogenic properties) with the designations 1A7, 4B5, and BEC-2. The 1A7 antibody is an anti-idiotype for ganglioside GD2, and is described in U.S. Pat. No. 5,612,030 and International Patent Application WO 96/22373. It was deposited with the American Type Culture Collection (ATCC), now located at 10801 University Blvd., Manassas Va. 20110-2209, USA, on Dec. 28, 1994 under Accession No. HB-11786. The 4B5 antibody is an anti-idiotype for ganglioside GD2, and is described in U.S. Pat. No. 5,653,977. The BEC-2 antibody is an anti-idiotype for ganglioside GD3, and is described in U.S. Pat. No. 5,529,922. Also of interest are the anti-GD2 anti-idiotypes of Cheung et al., and the anti-GM3 anti-idiotypes of Yamamoto et al., one of which was recombined by Hastings et al. as a chimera with human ogle κ constant region sequences.

Preferably, anti-idiotype antibody 1A7 (for a functional portion thereof, as described below) is used. 1A7 was raised against the anti-GD2 monoclonal antibody designated 14G2a.

The 1A7 antibody can be prepared in several ways. It is most conveniently obtained from the hybridoma deposited with the ATCC under Accession No. HB-11786, or the progeny thereof. For example, the cells can be cultured in a suitable medium, and spent medium can be used as an antibody source. Optionally, matrix-coated channels or beads and cell co-cultures may be included to enhance growth of antibody-producing cells. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal is optionally primed for ascites production by prior administration of a suitable composition; for example, Pristane.

Alternatively, 1A7 can be chemically synthesized in conjunction with standard methods of protein synthesis. A suitable method is the solid-phase Merrifield technique. Automated peptide synthesizers are commercially available, such as those manufactured by Applied Biosystems, Inc. (Foster City, Calif.).

1A7 may also be obtained by employing routine recombinant methods such as described in Sambrook et al. (1989). For instance, using the sequences and information provided herein, a polynucleotide encoding either the 1A7 heavy or light chain can be cloned into a suitable expression vector (which contains control sequences for transcription, such as a promoter). The expression vector is in turn introduced into a host cell. The host cell is grown under suitable conditions such that the polynucleotide is transcribed and translated into a protein. Heavy and light chains of 1A7 may be produced separately, and then combined by disulfide bond rearrangement. Alternatively, vectors with separate polynucleotides encoding each chain of 1A7, or a vector with a single polynucleotide encoding both chains as separate transcripts, may be transfected into a single host cell which may then produce and assemble the entire molecule. Preferably, the host cell is a higher eukaryotic cell that can provide the normal carbohydrate complement of the molecule. The 1A7 thus produced in the host cell can be purified using standard techniques in the art. A polynucleotide encoding 1A7 for use in the production of 1A7 by any of these methods can in turn be obtained from the hybridoma producing 1A7, or be produced synthetically or recombinantly from the DNA sequence provided herein.

Methods of antibody isolation are well known in the art. See, for example, Harlow and Lane (1988) *Antibodies: A Laboratory Manual,* Cold Spring Harbor Laboratory, New York. The 1A7 antibody is a mouse immunoglobulin of the IgG1 subclass, and may be isolated by any technique suitable for immunoglobulins of this isotype. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin. 1A7 may also be purified on affinity columns comprising the 14G2a paratope; for example, in the form of a purified Ab1 or Ab3. Preferably, 1A7 is purified from BALB/c ascites using Protein-A-CL-SEPHAROSE™ 4B chromatography followed by chromatography on a DEAE-SEPHAROSE™ 4B ion exchange column.

Alternatively, an active portion (see above under description of "anti-idiotype" or "anti-idiotype moiety") of 1A7 may be used, which comprise a portion of or an entire variable region of 1A7. Examples of variable region (whether intact or fragments) constructs have been provided above. FIGS. 2 and 3 provide the polypeptide sequences of the light and heavy chain variable regions as well as the polynucleotide sequences encoding the variable regions. Preparation of these 1A7 polypeptides employs standard techniques, such as recombinant techniques, in the art.

1A7 polypeptides can be produced by proteolytic or other degradation of 1A7, by recombinant methods (i.e., single or fusion polypeptides) as described above or by chemical synthesis. 1A7 polypeptides, especially shorter polypeptides up to about 50 amino acids, are conveniently made by chemical synthesis. Methods of chemical synthesis are known in the art and are commercially available. For example, a 1A7 polypeptide could be produced by an automated polypeptide synthesizer employing the solid phase method.

Preferably, the polypeptides are at least partially purified from other cellular constituents. Preferably, the polypeptides are at least 50% pure. In this context, purity is calculated as a weight percent of the total protein content of the preparation. More preferably, the proteins are 50–75% pure. More highly purified polypeptides may also be obtained and are encompassed by the present invention. For clinical use, the polypeptides are preferably highly purified, at least about 80% pure, and free of pyrogens and other contaminants. Methods of protein purification are known in the art and are not described in detail herein. Alternatively, if a 1A7 polypeptide(s) is expressed in a suitable storage medium, such as a plant seed, the 1A7 polypeptide need not be purified and could even be administered without purification. Fiedler et al. (1995) Biotechnology 13:1090–1093.

1A7 polypeptides can be obtained from intact 1A7, which can in turn be isolated from the hybridoma ATCC Accession No. HB-11786 producing 1A7, which is described in co-owned U.S. Pat. No. 5,612,030 and International Patent Application WO 96/22373. Techniques of isolating antibodies from hybridomas are well known in the art. See, e.g., Harlow and Lane (1988). Once intact 1A7 is obtained, 1A7 polypeptides can be obtained by degradation of intact 1A7, by using, for example, proteolytic enzymes (proteinases). Examples of proteolytic enzymes include, but are not limited to, trypsin, plasmin, and thrombin. Intact 1A7 can be incubated with one or more proteinases, or the digestions can be performed sequentially. The nature and extent of the proteolytic cleavage will depend upon the desired polypeptide length as well as the enzymes used. These techniques are well known in the art. Alternatively, or in addition, intact 1A7 can be treated with disulfide reducing agents to disassociate the molecule.

1A7 polypeptides can also be made by chemical synthesis using techniques known in the art. 1A7 polypeptides can also be made by expression systems, using recombinant methods. The availability of 1A7 polynucleotides encoding 1A7 polypeptides permits the construction of expression vectors encoding intact 1A7, functionally equivalent fragments thereof, or recombinant forms of 1A7. A polynucleotide encoding the desired 1A7 polypeptide, whether in fused or mature form, and whether or not containing a signal sequence to permit secretion, may be ligated into expression vectors suitable for any convenient host. Both eukaryotic and prokaryotic host systems can be used. The polypeptide is then isolated from lysed cells or from the culture medium and purified to the extent needed for its intended use. Purification or isolation of the polypeptides expressed in host systems can be accomplished by any method known in the art. For example, cDNA encoding intact 1A7 or a fragment thereof can be operatively linked to a suitable promoter, inserted into an expression vector, and transfected into a suitable host cell. The host cell is then cultured under conditions that allow transcription and translation to occur, and the desired polypeptide is recovered. Other controlling transcription or translation segments, such as signal sequences that direct the polypeptide to a specific cell compartment (i.e., for secretion), can also be used. Examples of prokaryotic host cells are known in the art and include, for example, *E. coli*. Examples of eukaryotic host cells are known in the art and include yeast, avian, insect, plant, and animal cells such as COS7, HeLa, CHO and other mammalian cells.

For scFv fragments, light and/or heavy chain variable regions are linked using a short linking peptide. Bird et al. (1998) Science 242:423–426. An example of a linking peptide is (GGGGS)$_3$(SEQ ID NO:5), which bridges approximately 3.5 nm between the carboxy terminus of one variable region and the amino terminus of the other variable region. Linkers of other sequences have been designed and used. Bird et al. (1988). Usually the linkers are selected to have little to no immunogenicity. For asymmetrical linkers, the scFvs can be assembled in any order. Generally, the entire variable regions are included in the scFv, which may be produced either recombinantly or synthetically.

Another illustration of a composition suitable for eliciting a specific immunological response against a target antigen in psoriasis is an expression vector encoding a polypeptide which is used in an immunogenic composition. The polypeptide encoded by the vector is either one comprising the antigenic determinant that is aberrantly expressed in psoriatic tissue, or else an anti-idiotype for the aberrantly expressed determinant. The encoding region is linked in the vector to suitable transcription and translation control elements that permit the encoding region to be expressed in the intended subject upon administration.

Vaccines made up of naked polynucleotides are generally described in Tang et al. (1992) Nature 356: 152–154. Viral vectors are also suitable, including by way of example, vectors based on herpes viruses, hepadna viruses, Sindbis virus, pseudotype retroviral vectors, adenovirus, adeno-associated virus. Where the encoding region encodes an anti-idiotype, of particular interest are vectors based on vaccinia virus that can be used in vaccine preparations (Moss (1991) Science 252:1662–1667). Such vectors can be constructed, for example, by homologous recombination of vaccinia plasmids and wild-type WR strain of vaccinia virus using CV-1 cells, according to the procedure of Mackett et al. (DNA Cloning, Vol. II, D. M. Glover, ed., IRL Press 1985).

Formulation of Therapeutic Compositions

The preparation of pharmaceutical compositions is conducted in accordance with generally accepted procedures for the preparation of pharmaceutical preparations. See, for example, *Remington's Pharmaceutical Sciences* 18th Edition (1990), E. W. Martin ed., Mack Publishing Co., Pa. Depending on the intended use and mode of administration, processing optionally includes sterilizing, mixing with appropriate non-toxic and non-interfering components, dividing into dose units, or enclosing in a delivery device.

Protein vaccines used in this invention typically comprise an adjuvant, which may be the same as or in addition to the excipient or carrier. Examples of adjuvants include but are not limited to aluminum hydroxide, alum, QS-21 (U.S. Pat. No. 5,057,540), DHEA (U.S. Pat. Nos. 5,407,684 and 5,077,284) including its precursors and modified forms (e.g., DHEA-S, the sulfonated form of DHEA), $\beta 2$ microglobulin (WO 91/16924), muramyl dipeptides, muramyl tripeptides (U.S. Pat. No. 5,171,568), monophosphoryl lipid A (U.S. Pat. No. 4,436,728; WO 92/16231) and its derivatives, such as various forms and generations of DETOX™ and BCG (U.S. Pat. No. 4,726,947). Other suitable adjuvants are aluminum salts, squalene mixtures (SAF-1), muramyl peptide, saponin derivatives, mycobacterium wall preparations, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) Nature 344:873–875. For veterinary use and for production of antibodies in animals, complete and incomplete Freund's adjuvant can be used. A preferred vaccine composition for peptides and anti-idiotypes or peptide derivatives thereof is prepared by mixing with aluminum hydroxide and incubated to about 48° C. for about 30 min.

Especially preferred adjuvants include QS-21 and RIBI™PC. The QS-21 molecule consists of a triterpene glycoside with the general structure of a quillaic acid 3,28-O-bis glycoside. There are two structural isomers designated V-1 and 2-1 at a typical ratio of ~2:1, both of which have adjuvant activity. QS-21 has been shown to stimulate a response against T-dependent antigens and unconjugated T-independent antigens. QS-21 also augments the induction of MHC Class I cytotoxic T lymphocytes to subunit antigen vaccines, as well as antigen-specific cellular proliferation. Preclinical trials confirm its safety and efficacy at 100 µg/dose. QS-21 is supplied by Aquila Biopharmaceutical, Inc. in Worchester, Mass.

The composition can optionally also contain other active medicinal agents, and/or non-active ingredients such carriers, and auxiliary substances such as wetting or emulsifing agents, and pH buffering agents. Additives of particular interest are adjuncts that enhance the immunogenic effect, such as mitogens or stimulatory cytokines. Of particular interest as adjunctive agents for anti-idiotype compositions are interleukins, particularly IL-2. The composition is typically formulated in liquid form, but can also be freeze-dried for reconstitution by hydration.

The route of administration is selected according to the formulation of composition and the intended effect. In the more usual embodiments of this invention, the composition is formulated and administered so as to stimulate a systemic response in the subject. With this in view, possible routes of administration include intracutaneous, subcutaneous, intramuscular, intraperitoneal, intradermal, oral, intranasal, intradermal, and intrapulmonary (i.e., by aerosol). Protein vaccines of this invention for human use are typically administered by a parenteral route, most preferably subcutaneous. A series of injections is preferably given at different subcutaneous sites.

In other embodiments, the composition is formulated and administered to produce a local effect (i.e., is formulated for topical administration). These compositions are generally used to boost at an affected site a response in an individual where a systemic immunological response against the target antigen has already successfully been induced, although pre-generation of a systemic immune response is not required. In these embodiments, the composition is generally in the form of a cream or gel, or other combination of the active ingredient and a readily absorbable or evaporable excipient. The composition is then administered on the skin at the affected site. Accordingly, the invention provides topical formulations of any of the target antigen (antigenic determinants) described herein, such as gangliosides, anti-idiotype moieties (i.e., anti-idiotype moieties, including anti-idioptype antibodies, for any of the gangliosides described herein), and the expression vectors described herein. Preferably, a topical formulation comprises 1A7. Examples of suitable topical formulations, which are well known in the art, include ointments, creams, and gels.

In certain embodiments of the invention, the composition is specially designed for psoriasis, comprising a formulation and dose that is designed especially to maximize management of the psoriatic condition. In other embodiments, the composition is formulated in a similar fashion as it would be for use in another type of therapy, such as for cancer treatment, that shares a common objective, such as the eliciting of an immunological response against an antigen that is aberrantly expressed in either condition.

Preferably, compositions useful for treating psoriasis according to the present invention are accompanied by written instructions as part of the packaging or in a product insert. The written instructions can simply indicate that psoriasis (in any one of its many forms) is a suitable indication for the use of the composition. Optimally, the instructions will also indicate suitable subjects and conditions, the recommended route of administration, timing, and dosage, contraindications, potential side effects, and expected benefit.

The invention accordingly provides a composition for use (or use of any of the compositions described herein) in the preparation of a medicament for use in the treatment of psoriasis. These compositions comprise any of the embodiments described herein. In one embodiment, the invention provides use of a component selected from the group consisting of i) a ganglioside; ii) an anti-idiotype moiety for a ganglioside; and iii) an expression vector encoding an anti-idiotype for a ganglioside in the manufacture of a medicament for the treatment of psoriasis. The psoriasis to be treated may be any of gluttate psoriasis, pustular psoriasis, plaque-type psoriasis, psoriatic arthritis, and/or chronic plaque psoriasis. The ganglioside may be any of GM2, GM3, GD1B, GD2, 9-O-acetyl GD2, GD3, GD3 lactone, 9-O-acetyle GD3, and GT3. The anti-idiotype moiety may be any of 1A7, 4B5, or BEC-2, and is preferably 1A7.

Use of Therapeutic Compositions

Patients suitable for treatment according to this invention have clinical or histological features of psoriasis, particularly gluttate psoriasis, pustular psoriasis, plaque-type psoriasis, or psoriatic arthritis. The compositions can also be given to patients who have no outward signs of psoriasis, but are at risk for developing the disease especially in its more severe manifestations (because of a genetic predisposition, family history or previous manifestations), although this is less typical. Since the effectiveness of this invention is believed to involve a host immunological response against the target antigen, the therapeutic compositions are predicted to be more effective when the individual is not immunodeficient or immunocompromised due to a genetic abnormality, infection, or by chemical treatment.

The amount of the immunogenic substance administered at one time is selected with a view to clinical safety, and to achieve the initial desired immunological and clinical result within a few administrations. The range of effective concentrations for protein immunogens is generally about 10 $\mu$g to 20 mg, and typically 200 $\mu$g to 10 mg, with the tendency towards higher values where the immunogenic determinant is a proportionately smaller part of the protein. The range of effective concentrations for polynucleotide vaccines is generally about 10 $\mu$g to 500 $\mu$g of nucleic acid, typically about 50 to 100 $\mu$g. Since clinical efficacy is believed to correlate with the extent of the specific immunological response obtained, a dose that is clinically effective can in principle be predicted by determining an immunogenic dose in an animal model, and then scaling the dose appropriately for human use. Administrations are typically conducted on a weekly or biweekly basis until there is evidence of an immunological or clinical response. Administration can then be continued on a less frequent basis, such as biweekly, monthly, or bimonthly as appropriate.

Treatment according to this description can optionally be combined with other regimens focused on clinical symptoms, including but not limited to local treatment with topical steroids, topical calcipotriol, or ultraviolet light; or systemic treatment with methotrexate, etretinate or cyclosporine. Parallel treatment can also be conducted with a view to activating the immune system to make it more responsive to the vaccine, such as simultaneous administration of a mitogen or cytokine. In one example, IL-2 is injected at a collateral site at a dose of about 1.5 to 15×10$^6$ U m$^{-2}$ day$^{-1}$, either throughout the priming phase of vaccine treatment, or as a pulse given a few consecutive days on a biweekly schedule, or any reasonable variation.

Clinical response is measured around about the time of administration and on regular follow-up. Immunological response can also be measured, if desired, by collecting periodic blood samples for analysis.

Presence of antibody activity (for example, against a particular ganglioside or a particular anti-idiotype) can be determined by standard immunoassay of serum or plasma samples from the treated subject. For anti-idiotype activity, the sample is preincubated with autologous immunoglobulin or adsorbed on a suitable affinity resin to remove antibody activity against isotypic and allotypic determinants. In one assay method, the sample is incubated in a microtiter plate well previously coated with the target antigen; the well is washed, and then the reaction is developed with an isotopically or enzymatically labeled anti-immunoglobulin reagent. Results are compared with those using preimmune serum or serum from subjects immunized with an unrelated antigen. Specificity can also be measured by Western blot. The antigen is separated by electrophoresis over a polyacrylamide gel, blotted onto nitrocellulose, and then developed with the sample. In an third example, the sample is incubated with cells that do or do not express the antigen of interest, and then developed using a fluorescently tagged anti-immunoglobulin. Staining frequency and intensity can then be measured by FACS analysis. A model cell line is one expressing GD2 is M21/P6. In a fourth example, the sample is overlaid onto a histological sample from a psoriatic lesion, as may be taken from the treated subject, and then developed with an enzyme-labeled anti- immunoglobulin. This is illustrated in Example 3. The nature of the response in the sample can be further characterized in any of these assays by competition with an antibody with known activity for the target antigen. A model antibody for GD2 is monoclonal antibody 14G2a.

Complement mediated cytotoxicity (CMC) can be measured, if desired, using a cell line that expresses the target antigen. The cell line is labeled with a cytosolic marker, such as $^{51}$Cr. The assay is conducted by adding and incubating a sample suspected of containing antibody. Complement is added in a suitable form, such as guinea pig serum pre-adsorbed with the cell line. After a suitable incubation period at 37° C., extent of $^{51}$Cr release is then measured and compared with that of unopsonized control cells. $^{51}$Cr labeled target cells can also be used to measure antibody-dependent cell-mediated cytotoxicity (ADCC) in the sample, by supplying human peripheral blood mononuclear cells (PBMC) from normal subjects as effector cells at a ratio of effector:target cells of about 100:1.

A cell mediated immune response in a subject can be measured by isolating PBMC from a blood sample of the treated subject, collected into heparinized tubes, and separated on a suitable gradient such as Ficoll-Hypaque™. To measure T cell proliferation (a general indicator of T cell activation against the antigen), the cells are incubated with a range of concentrations of the target antigen. A non-specific mitogen such as PHA serves as a positive control; incubation with an unrelated antigen serves as a negative control. After incubation of the PBMCs for an appropriate period (typically 5 days), [$^3$H]thymidine incorporation is measured, and the proliferating cells can be further characterized by flow cytometry using cell type specific markers. Cytotoxic T cell response can be measured after a period of stimulation by presenting with $^{51}$Cr labeled antigen-bearing target cells.

Clinical outcome is followed over the course of therapy for a therapeutic effect and undesirable side-effects, as illustrated in Example 4. Ideally, the compositions promote resolution of the clinical features, but stabilization of the condition is a satisfactory outcome. Progression or regression of the disease is followed according to the particular clinical manifestations of the original presentation, and typically includes the number and size of psoriatic lesions, and the extent of total body surface area that is involved. Status can also be measured at the microscopic level as the proportion of epidermal cell proliferation or the proportion of cells expressing target antigen.

The selection of the target antigen (or antigenic determinant) and the formulation of the immunogenic composition can be adjusted by the manufacturer, and the exact dose and timing for the administration can be adjusted by the administering physician, without departing from the spirit of the invention.

The invention also provides methods for preparing a composition for use in the treatment of psoriasis, comprising raising an anti-idiotype antibody against a monoclonal antibody that binds an antigenic determinant that is aberrantly expressed in psoriatic tissue, wherein the anti-idiotype antibody is capable of eliciting an immunological response in a human against the antigenic determinant. Alternatively, the methods comprise preparing an immunogenic composition comprising the aberrantly expressed determinant.

Screening Methods of the Invention

The invention also provides methods of screening immunogenic compositions for use in treatment of psoriasis in humans.

In some embodiments, the methods comprise the steps of (a) administering to a plurality of human subjects having psoriasis an immungenic composition comprising an immunogenic form of i) an antigenic determinant that is aberrantly expressed in psoriatic tissue; ii) an monoclonal anti-idiotype antibody for an antigenic determinant that is overexpressed in psoriatic tissue; or iii) an expression vector encoding either i) or ii); and (b) correlating the progression of the psoriasis in the human subjects treated in step (a) in relation to that ihn untreated human subjects having psoriasis, with the effectiveness of the immunogenic composition.

In other embodiments, the screening methods comprise the following steps: a) administering to a plurality of human subjects having psoriasis an immunogenic composition, comprising an immunogenic form of: i) an antigenic determinant that is aberrantly expressed in psoriatic tissue; ii) a monoclonal anti-idiotype antibody for an antigenic determinant that is aberrantly expressed in psoriatic tissue; or iii) an expression vector encoding either i) or ii); and b) determining the extent of an immunological response against the antigenic determinant in each subject treated in step a); and c) correlating the progression of the psoriasis in relation to the extent of the immunological response against the antigenic determinant in each subject with the effectiveness of the immunogenic composition.

In any of these screening embodiments, the antigen that is aberrantly expressed in psoriatic tissue may preferably be a ganglioside, more preferably GD2.

Kits of the Invention

The invention also provides kits comprising a) a composition packaged in a container and comprising an immunogenic form of a component selected from the group consisting of: i) a ganglioside; ii) an anti-idiotype for a ganglioside; and iii) an expression vector encoding an anti-idiotype for a ganglioside; and b) written instructions for using the composition in the treatment of psoriasis. Preferably, the component is 1A7.

The examples presented below are provided as a further guide to a practitioner of ordinary skill in the art, and are not meant to be limiting in any way.

EXAMPLES

Example 1

Demonstration of Ganglioside Antigen in Psoriasis Tissue

In this experiment, histology sections from psoriasis lesions were screened for the presence of aberrantly expressed antigens that would be suitable targets for an active vaccination strategy.

Skin-punch biopsies were obtained from patients having benign Psoriasiform Dermatitis. Paraffin blocks from three samples were cut into 5 $\mu$m cross-sections through the dermal layers. The sections were fixed onto slides and deparaffinized by a series of graduated washes of decreasing ethanol content. Once equilibrated into phosphate-buffered saline, pH 7.4, the sections were blocked against non-specific binding by overlaying with 10% normal rabbit serum that had been heat-inactivated.

After washing, the sections were overlaid with one of a panel of primary antibodies purified by anion exchange chromatography as required, and diluted to 50 $\mu$g/mL. The section was incubated with the primary antibody at room temperature for about an hour, and then rewashed. The section was next overlaid with biotinylated rabbit anti-mouse immunoglobulin as secondary antibody, incubated, and washed. The sections were developed using a streptavidin-peroxidase conjugate, followed by substrate.

The panel of primary antibodies consisted of the following:

Monoclonal antibody 14G2a, grown from a hybridoma cell line obtained from the Scripps Research Institution. 14G2a has been subtyped as an IgG2aκ. 14G2a is specific for the ganglioside antigen GD2, and does not bind to gangliosides GM1, GM2, GM3, GD3, or GT1b. The ability of 14G2a to bind GD2 in fixed tissue was confirmed by immunoperoxidase staining of paraffin blocks of human melanoma tissue. 14G2a also specifically binds the GD2 positive melanoma cell line M21/P6 when used as the primary antibody in FACS analysis.

Monoclonal antibody 8019, produced from the hybridoma obtained from the American Type Culture Collection (ATCC, Rockville Md.). 8019 has been subtyped as an IgG1κ, and is specific for carcinoembryonic antigen (CEA). The ability of 8019 to bind CEA in fixed tissue was confirmed by immunoperoxidase staining of paraffin blocks of human colon cancer samples. 8019 also specifically binds the CEA positive colon cancer cell line LS174-T when used as the primary antibody in FACS analysis.

Monoclonal antibody MC-10, also designated BrE-1, is specific for human milk fat globule (HMFG), an antigen aberrantly expressed in breast cell carcinomas. MC-10 has been subtyped as an IgG2bκ. The ability of MC-10 to bind HMFG in fixed tissue sections was confirmed by immunoperoxidase staining of paraffin blocks of human breast cancer samples. MC-10 also specifically binds the HMFG positive breast cancer cell lines MCF-7 and SKBR3 when used as the primary antibody in FACS analysis.

A monoclonal mouse IgG2b of unknown specificity, purchased from Sigma Chemical Co., serving as a negative control.

Staining intensity was graded on a scale of (−) to (++++). The following results were obtained:

TABLE 1

Immunohistochemical staining for aberrantly expressed antigen

| Primary Antibody | Staining Intensity | | |
|---|---|---|---|
| | Sample 1 | Sample 2 | Sample 3 |
| 14G2a | +++ | +++ | +++ |
| 8019 | ++++ | ++++ | ++++ |
| MC10 | ± | ± | ± |
| mouse IgG2b control | − | − | − |
| PBS | − | − | − |

Both 14G2a and 8019 antibodies gave strong staining in all samples tested. The staining pattern was consistent with specific staining for affected tissue, since only dermal layers were stained. Monoclonal antibody MC10 was essentially negative.

These results indicate that both GD2 and CEA are candidate targets for a vaccine strategy against psoriasis.

Example 2

Eliciting an Anti-GD2 Response in Humans using an Anti-idiotype

Hybridoma cells expressing monoclonal anti-idiot antibody 1A7 (U.S. Pat. No. 5,612,030) were used for the production of ascites fluid. 9.7 g of purified antibody was prepared by TSD BioServices under GMP-conditions. The regulatory testings on the antibody preparation were completed according to FDA guidelines. This example describes how the antibody is tested in a human clinical study to verify safety and demonstrate its ability to elicit an anti-GD2 response in humans.

Patients are immunized with 1A7 antibody mixed with 100 µg of QS-21 adjuvant. Patients are randomized to one of the four dose levels. The total number of patients is between about 12 and 32. Injections are given biweekly for four total doses, or until an immune response is observed. Therapy continues with monthly injections until tumor progression is found. Patients are monitored carefully for anaphylaxis, serum sickness, and other potential side effects.

Periodic blood samples are obtained to determine the effect on hematopoietic cells as well as renal and hepatic function. All patients entered into the study undergo leukapheresis prior to the first immunization (pre-therapy). In addition, blood samples are obtained prior to each injection of 1A7 to determine serum levels of Ab3 and Ab1' antibodies and cytotoxic T cell responses. The specificity of the humoral responses is confirmed by immune flow cytometry, radioimmunoassay, and dot blot analysis. Antiglobulin responses to the murine antibody is tested by sandwich radioimmunoassay. Sera are also tested for an ability to inhibit the binding of anti-GD2 mAb to GD2 antigen. The immune profile of patients is further assessed by testing the proliferative response of patient's lymphocytes to anti-idiotype antibody, purified GD2 antigen, and irradiated tumor cells and the cytotoxicity of patient's lymphocytes for GD2-positive HLA-matched cell lines or autologous tumor cells (where possible).

What follows are the results from seven participating in the study over a sufficient period to evaluate the presence of an immunological response. Each patient was immunized with 1 mg, 2 mg, 4 mg, or 8 mg of antibody 1A7 in QS-21 on a biweekly schedule. For the first few patients in the study, the first 2 to 4 doses were given intramuscularly, and periodic serum samples were collected to determine the presence of human anti-mouse (HAMA) activity and anti-1A7 activity. Titers were low, and it was decided to continue the course of immunization subcutaneously. All patients seroconverted positive with respect to both HAMA and anti-1A7, as determined by immunoassay. The response comprised specific Ab3 activity, as demonstrated by the ability of each serum to inhibit the binding of radiolabeled 1A7 to solid-phase linked 14G2a (Ab1). None of the patients have yet shown objective clinical responses related to their cancer. However, three of the seven patients (270+ to 510+ days) have stable disease and continue on vaccine therapy.

The results demonstrate that administration of 1A7 as a pharmaceutical composition with the adjuvant QS-21 is very well tolerated up to a dose of 8 mg, and is highly effective in generating an anti-GD2 response.

To investigate the nature of the response further, anti-1A7 antibody was affinity purified from the sera of four of the patents. First, each sample was passed over a column of 14G2a antibody, eluted with a glycine buffer (pH~2.5), and exchanged into PBS. Next, HAMA activity that was not Ab3 was depleted by negative selection on a mouse immunoglobulin adsorbant. The amount of specific anti-1A7 (Ab3) obtained was as follows: Patient 1 (administered 1 mg 1A7 per dose), yield 0.67 mg Ab3 from 10 mL serum. Patient 2 (administered 2 mg 1A7 per dose), yield 1.32 mg Ab3 from 10 mL serum. Patient 3 (administered 4 mg 1A7 per dose), yield 1.71 mg Ab3 from 10 mL serum. Patient 4 (administered 4 mg 1A7 per dose), yield 0.73 mg Ab3 from 10 mL serum. This indicates that a substantial amount of Ab3 is produced as a result of administering 1A7 at any of the doses tested, and apparently is in molar excess of antigen in the circulation.

The affinity and specificity of the response to GD2 was further confirmed by using the affinity purified Ab3 in several of the assay systems described earlier. In one test, an assay plate was coated with ganglioside GD2 or GD3, overlaid with purified Ab3, and then developed with alkaline phosphatase labeled anti-immunoglobulin. The results showed that each patient's response comprises the production of anti-GD2 antibody (Ab1')., but not anti-GD3 antibody. In another test, an assay plate was coated with GD2, overlaid with purified Ab3, and then developed with isotype-specific anti-immunoglobulin reagents. The anti-GD2 response was apparently a mature response comprising both IgG and IgM, with IgG predominating.

Inhibition titration experiments were conducted using purified Ab3 from three different patients. In one test, an assay plate was coated with ganglioside GD2, and varying amounts of purified Ab3 were tested for the ability to inhibit the binding of radiolabeled 14G2a (Ab1). The half-titration point for each Ab3 was comparable to that of unlabeled 14G2a. In another test, varying amounts of purified Ab3 were tested for their ability to inhibit the binding of radio-labeled 14G2a to the GD2-expressing murine lymphoma cell line EL4. The results indicated that the Ab3 induced by administration of 1A7 competes for binding to GD2 aberrantly expressed by model target cells.

Example 3

Demonstration of Antibody to Psoriasis-associated Antigen in the Serum of Immunized Human Subjects Ab3 affinity purified-from the sera of human patients treated with an anti-idiotype were tested for the presence of circulating antibody against a psoriasis associated antigen.

Patients were treated with monoclonal anti-idiotype 1A7 (an anti-idiotype for GD2), or with anti-idiotype 3H1 (an anti-idiotype for CEA). Treatment of subjects with 1A7 is described in Example 2. The preparation and use of 3H1 is described in PCT patent applications WO 96/20219 and WO 96/20277.

After a course of multiple immunizations on a biweekly immunization schedule, the respective Ab3 present in were prepared by passing immune sera over an affinity column made of the immunizing antibody, and recovering the bound fraction. As a negative control, normal or preimmune human IgG was prepared by passing serum of an unimmunized subject over a Protein G column.

The purified IgG fractions were then tested for their ability to specifically stain affected psoriasis tissue, using the immunohistochemical methods described in Example 1. The results are shown in the following Table:

TABLE 2

Tissue staining by antibody present in the sera of immunized patients

| | Staining Intensity | | | |
|---|---|---|---|---|
| Primary Antibody | Sample 1 | Sample 2 | Sample 3 | Sample 4 |
| 14G2a (Ab1 for 1A7; positive control) | +++ | +++ | +++ | +++ |
| Ab3 from patients treated with 1A7 | ++++ | ++++ | ++++ | ++++ |
| normal human IgG | – | – | – | – |
| Ab3 from patients treated with 3H1 | – | – | – | – |

The results show that treatment of human patients with monoclonal antibody 1A7 successfully elicits an active immune response that is specific for a target antigen on affected psoriasis tissue. The target antigen is shared between different psoriasis patients, and (in view of the known immunogenic properties of the 1A7 antibody) most probably is GD2. Specificity is confirmed by two additional observations: a) the staining pattern with Ab3 from the 1A7 treated subject showed staining of the affected skin cells but not surrounding muscle fibers; b) anti-idiotype antibody 3H1 raises a specific Ab3 response, but the response was apparently not specific for psoriasis tissue.

Example 4
Treating Psoriasis by Eliciting an Active Anti-ganglioside Immunological Response Psoriasis afflicts approximately 1 to 2 percent of the adult population in various forms. Patients with extensive plaque psoriasis and pustular psoriasis frequently require systemic therapy. Topical steroids, topical calcipotriol, or ultraviolet light may not give adequate control. The currently used systemic medications such as methotrexate, etretinate and cyclosporine are sometimes effective, but associated with significant side effects.

A patient with advanced psoriasis was administered monoclonal antibody 1A7 as part of a clinical trial for the treatment of melanoma. After leaving the trial, the patient returned to the attending physician (Dr. K. Foon) and reported that his psoriatic systems, which had previously been persistent, had improved. His case history and results of the immunological tests were reviewed, and it was discovered that the resolution of the symptoms correlated with the stimulation of an anti-GD2 immune response (as detected in serum) during his treatment with 1A7 in the melanoma trial. Subsequently, psoriasis tissue samples from several patients were evaluated by immunohistochemistry (Example 1), and all were positive for an antigen recognized by anti-GD2 antibody. Antibody present in the serum of several patients immunized with the GD2 anti-idiotype 1A7 was isolated, and found to react with a target antigen on psoriatic tissue (Example 3).

This example provides a method for testing the efficacy of raising an anti-GD2 immunological response in the treatment of psoriasis.

Fifteen patients who have been diagnosed with severe chronic plaque psoriasis, and who have had an unsatisfactory response to a prior systemic therapy, topical steroids or ultraviolet light are treated. Eligibility criteria also include absence of active infection or blood-born disease, adequate renal and hepatic function tests, granulocyte count$\geq$1000 $mm^{-3}$, platelets>100,000 $mm^{-3}$, absence of allergy to mouse protein, and ability to provide informed consent. Subjects are pre-screened for the presence of GD2 antigen on keratinocytes in psoriatic lesions by immunohistology, as exemplified in Example 1.

FIG. 1 shows the scheme of treatment. The admitted patients are treated with 2 mg of 1A7, mixed with 100 $\mu$g of the adjuvant QS-21. Four injections are given initially, one every other week, and then injections are given monthly. Treatment is stopped if there is a significant adverse event, if there is substantial advancement of the disease, or if there is no significant effect after six months. Patients who show advancement of the disease are followed for an additional six months after the cessation of treatment. Patients with stable or improved disease six months after initiation of treatment receive further treatment for an additional six months, followed by another evaluation.

During the course of the trial, patients are monitored for toxicity. Periodic blood samples are taken to determine any effect on hematopoietic cells, renal and hepatic function, LDH, and uric acid. The most likely side effects are local skin reaction, fever, chilling, and sweating, seldom requiring therapy and persisting for only a few hours. Anti-pruritics are used where needed. Allergic reactions are treated symptomatically with diphenhydramine or hydroxyzine. Bronchospasm and anaphylaxis, if they occur, are treated with epinephrine and supportive care, and result in removal of the patient from the treatment regimen. In view of previous tests of 1A7 in cancer patients (Example 2), major toxicity is not anticipated.

Periodic blood samples are also taken to follow the immunological response in each patient. The presence of antibodies against 1A7 (the Ab3 response) and against GD2 (the Ab1' response) is measured by standard plate-binding immunoassay. Serum or isolated Ab3 is also tested for binding to GD2 expressed on tumor cell lines or psoriatic tissue. Antibody-dependent cellular cytotoxicity, T cell proliferative activity, or cytotoxic T cell activity may also be measured according to the procedures described elsewhere in this disclosure. Induction of both humoral and cellular anti-GD2 activity is anticipated in the majority of treated subjects after four or more injections with the 1A7 vaccine.

Results are determined as follows. Symptoms are graded according to the Psoriasis Area and Severity Index. Severity is graded on a numerical scale (0=none; 1=slight; 2=moderate; 3=severe), taking into account erythema, scaling, and induration. The extent is based on total body surface involvement (trunk=35%; legs=35%; arms=20%; head and neck=10%). Progression is then graded between –1 and +3 (–1=worse; 0=stable; +1=minimal improvement; +2=definite improvement; +3=clearing). Clinical experience is that without treatment, the disease will typically progress, involving more surface or having plaques with more erythema and induration. The treatment is considered to be successful if there is substantial improvement or stabilization of the disease, compared to the typical course in patients not treated with the vaccine, and initially presenting with similar symptoms and clinical experience.

Although the foregoing invention has been described in some detail by way of illustration and example for purposes of clarity and understanding, it will be apparent to those skilled in the art that certain changes and modfications will be practiced. Therefore, the description and examples should not be construed as limiting the scope of the invention, which is delineated by the appended claims.

NON-COMPREHENSIVE LIST OF REFERENCES CITED

1. Beardsley T. Crabshoot. Manufacturers gamble on cancer vaccines—again. Scientific American p. 102, September 1994.
2. Bhattacharya-Chatterjee, M. et al. Idiotype vaccines against human T cell acute lymphoblastic leukemia. I. Generation and characterization of biologically active monoclonal anti-idiotypes. J. Immunol. 139:1354–1360, 1987.
3. Chattopadhyay P. et al. Murine monoclonal anti-idiotype antibody breaks unresponsiveness and induces a specific antibody response to human melanoma-associated proteoglycan antigen in cynomolgus monkeys. Proc. Natl. Acad. Sci. USA 89:2684–2688, 1992.
4. Cheresh, D. A. et al. Biosynthesis and expression of the disialoganglioside GD2, a relevant target antigen on small cell lung carcinoma for monoclonal antibody-mediated cytolysis. Cancer Res. 46:5412–5118, 1996.
5. Cheung, N-K. V. et al. Ganglioside GD2 specific monoclonal antibody 3F8. A Phase I study in patients with neuroblastoma and malignant melanoma. J. Clin. Oncol. 5:1430–1440, 1987.
6. Cheung, N.-K. V. Canete, A. Cheung, I. Y. Ye, J.-N. and Liu, C. Disialoganglioside $G_{D2}$ anti-idiotypic monoclonal antibodies. Int. J. Cancer 54:499–505, 1993.
7. Conry R M et al. A carcinoembryonic antigen polynucleotide vaccine for human clinical use. Cancer Gene Ther. 2:33–38, 1995.
8. Denton G. W. et al. Clinical outcome of colorectal cancer patients treated with human monoclonal anti-idiotypic antibodies. Int. J. Cancer 57:10–14, 1994.
9. Hamilton W. B. et al. Gangliosides expression on human malignant melanoma assessed by quantitative immune thin layer chromatography. Int. J. Cancer 53:1 ff. 1993.
10. Hastings, A. Morrison S. L. Kanada S. Saxton, R. E. and Irie, R. F. Production and characterization of a murine/human chimeric anti-idiotype antibody that mimics ganglioside. Cancer Res. 52:1681–1686, 1992.
11. Hawkins, R. E. et al. A genetic approach to idiotypic vaccination. J. Immunother. 14:273–278, 1993.
12. Heidenheim M. et al. CDw60, which identifies the acetylated form of $G_{D3}$ gangliosides, is strongly expressed in human basal cell carcinoma. Br. J. Dermatol. 133:392, 1995.
13. Herlyn D. et al. Cloned antigens and anti-idiotypes. Hybridoma 14:159–166, 1995.
14. Liang P. et al. Differential display of eukaryotic messenger RNA by means of the polymerase chain reaction. Science 257:967–971, 1992.
15. Liang P. et al. Recent advances in differential display. Curr. Opin. Immunol. 7:274–280, 1995.
16. Livingston, P. O. Construction of cancer vaccines with carbohydrate and protein (peptide) tumor antigens. Curr. Opin. Immunol. 4:624–629, 1992.
17. Livingston, P. O. Approaches to augmenting the immunogenecity of melanoma gangliosides: From whole melanoma cells to ganglioside-KLH conjugate vaccines. Immunol. Review, 145:147–166, 1995.
18. Mittelman A. et al. Human high molecular weight melanoma-associated antigen (HMW-MAA) mimicry by mouse anti-idiotypic monoclonal antibody MK2-23: Induction of humoral anti-HMW-MAA immunity and prolongation of survival in patients with stage IV melanoma. Proc. Natl. Acad. Sci. USA 89:466–470, 1992.
19. O'Boyle K. P., Zamore R., Adluri S., Cohen A., Kemeny N., Welt S., Lloyd K. O., Oettgen H. F., Old L. J., and Livingston P. O. Immunization of colorectal cancer patients with modified ovine submaxillary gland mucin and adjuvants induces IgM and IgG antibodies to sialylated Tn. Cancer Res. 1992. (Reference 17 of Livingston, 1992).
20. Offner H. et al. Lymphocyte stimulation by gangliosides, cerebrosides and basic protein in juvenile rheumatoid arthritis. J. Clin. Lab. Immunol. 6:35–37, 1981.
21. Paller A. S. et al. Absence of a stratum corneum antigen in disorders of epidermal cell proliferation: detection with an anti-ganglioside GM3 antibody. J. Invest. Dermatol. 92:240–246, 1989.
22. Paller A. S., Arnsmeier S. L., Alvarez-Franco M., and Bremer E. G. Ganglioside GM3 inhibits the proliferation of cultured keratinocytes. J. Invest. Dermatol. 100:841–845, 1993.
23. Pardoll D. New strategies for active immunotherapy with genetically engineered tumor cells. Curr. Opin. Immunol. 4:619–23, 1992
24. Progenics Pharmaceuticals, Inc. Prospectus for sale of 2,000,000 shares of Common Stock subject to completion, dated Oct. 30, 1996.
25. Saleh M. N. Stapleton, J. D. Khazaeli M. B. and LoBuglio, A. F. Generation of a human anti-idiotypic antibody that mimics the GD2 antigen. J. Immunol. 151:3390–3398, 1993.
26. Samonigg H. et al. Immune response to tumor antigens in a patient with colorectal cancer after immunization with anti-idiotype antibody. Clin. Immunol. Immunopathol. 65:271–277, 1992.
27. Skov L. et al. Lesional psoriatic T cells contain the capacity to induce a T cell activation molecule CDw60 on normal keratinocytes. Am. J. Pathol. 150:675–683, 1997.
28. Sunday M. E. et al. Differential display RT-PCR for identifying novel gene expression in the lung, Am. J. Physiol. 269:L273–L284, 1995.
29. Yamamoto S. Yamamoto T. Saxton R. E. Hoon D. S. B. and Irie, R. F. Anti-idiotype monoclonal antibody carrying the internal image of ganglioside GM3. J. Natl. Cancer Inst. 82:1757–1760, 1990.

| | | |
|---|---|---|
| U.S. Pat. No. 5,053,224 | E. C. DeFreitas et al. | Anti-idiotype vaccines |
| U.S. Pat. No. 5,102,663 | P. O. Livingston et al. | Vaccines for 9-O-acetyl GD3 |
| U.S. Pat. No. 5,141,742 | J. P. Brown et al. | p97 vaccines against melanoma |
| U.S. Pat. No. 5,308,614 | Hakomori et al. | Anti-tumor associated gangliosides |
| U.S. Pat. No. 5,330,977 | E. Tubaro et al. | Losoganglioside derivatives |
| U.S. Pat. No. 5,529,922 | P. B. Chapman et al. | GD3 anti-idiotype vaccine |
| U.S. Pat. No. 5,612,030 | M. Chatterjee et al. | GD2 anti-idiotype vaccine |
| U.S. Pat. No. 5,653,977 | M. N. Saleh | GD2 anti-idiotype vaccine |
| BE 1008391 | A. Remacle | CEA vaccine |

| | | | |
|---|---|---|---|
| EP 0443518 | Y. Nagai et al. | Episialo ganglioside pharmaceuticals | |
| EP 0661061 | R. P. Rodriguez et al. | N-glycolylated ganglioside vaccines | |
| JP 6145069 | Nisshin Oil Mills Ltd. | Ganglioside angiogenesis inhibitors | |
| WO 9219266 | J. Kanton et al. | CEA vaccinia vaccine | |
| WO 93/10134 | H. Magnusson et al. | Ganglioside lactam analogues | |
| WO 94/16731 | Livingston et al. | Ganglioside-KLH vaccines with QS-21 | |
| WO 95/04548 | A. Maida et al. | Prostate cancer vaccines | |
| WO 96/20277 | M. Chatterjee et al. | CEA anti-idiotype vaccines | |
| WO 96/20219 | M. Chatterjee et al. | CEA anti-idiotype vaccines | |
| WO 96/22373 | M. Chatterjee et al. | GD2 anti-idiotype vaccines | |
| WO 97/22694 | M. Chatterjee et al. | HMFG anti-idiotype vaccines | |

What is claimed is:

1. A method for treating psoriasis in an individual, comprising administering a composition comprising antibody 1A7, which is produced by a hybridoma cell line deposited at the American Type Culture Collection (ATCC) as Accession No. HB-11786, or progeny thereof, wherein said progeny produce an antibody having all of the identifying characteristics of monoclonal antibody 1A7 produced by the deposited hybridoma cell line, wherein an immunological response specific for GD2 is elicited in the individual.

2. A method for treating psoriasis in an individual, comprising administering a composition comprising a polypeptide comprising a light chain variable region amino acid sequence contained in SEQ ID NO:2, and a heavy chain variable region amino acid sequence contained in SEQ ID NO:4, wherein an immunological response specific for GD2 is elicited in the individual.

3. The method of claim 1 or 2, wherein the immunological response comprises production of anti-GD2 antibody.

4. The method of claim 1 or 2, wherein the immunological response comprises production of GD2-specific T cells.

* * * * *

SEQUENCE LISTING

```
<160> NUMBER OF SEQ ID NOS: 5

<210> SEQ ID NO 1
<211> LENGTH: 447
<212> TYPE: DNA
<213> ORGANISM: Mus Musculus
<220> FEATURE:
<221> NAME/KEY: CDS
<222> LOCATION: (1)..(447)
<221> NAME/KEY: mat_peptide
<222> LOCATION: (58)..(447)

<400> SEQUENCE: 1 atg aag ttg cct gtt agg ctg ttg gtg ctg atg ttc tgg att cct gct      48
Met Lys Leu Pro Val Arg Leu Leu Val Leu Met Phe Trp Ile Pro Ala
            -15                 -10                  -5 tcc agc gat gat gtt ttg atg acc caa act cca ctc tcc ctg cct gtc      96
Ser Ser Asp Asp Val Leu Met Thr Gln Thr Pro Leu Ser Leu Pro Val
         -1   1                 5                     10 agt ctt gga gat caa gcc tcc atc tct tgc aga tct agt cag agc att     144
Ser Leu Gly Asp Gln Ala Ser Ile Ser Cys Arg Ser Ser Gln Ser Ile
         15                 20                  25 gta cat agt aat gga aac acc tat tta gaa tgg tac cta cag aaa cca     192
Val His Ser Asn Gly Asn Thr Tyr Leu Glu Trp Tyr Leu Gln Lys Pro
 30                 35                  40                  45 ggc cag tct cca aac ctc ctg atc tac ttt gtt tcc aac cga ttt tct     240
Gly Gln Ser Pro Asn Leu Leu Ile Tyr Phe Val Ser Asn Arg Phe Ser
                 50                  55                  60 ggg gtc cca gac agg ttc agt ggc agt gga tca ggg aca gat ttc aca     288
Gly Val Pro Asp Arg Phe Ser Gly Ser Gly Ser Gly Thr Asp Phe Thr
             65                  70                  75 ctc aag atc agc aga gtg gag gct gag gat ctg gga gtt tat tac tgc     336
Leu Lys Ile Ser Arg Val Glu Ala Glu Asp Leu Gly Val Tyr Tyr Cys
         80                  85                      90 ttt caa ggt tca cat gtt ccg tgg acg ttc ggt gga ggc acc aag ctg     384
Phe Gln Gly Ser His Val Pro Trp Thr Phe Gly Gly Gly Thr Lys Leu
     95                 100                 105 gaa atc aaa cgg gct gat gct gca cca act gta tcc atc ttc cca cca     432
Glu Ile Lys Arg Ala Asp Ala Ala Pro Thr Val Ser Ile Phe Pro Pro
110                 115                 120                 125 tcc agt aag ctt ggg                                                  447
Ser Ser Lys Leu Gly
```

-continued

```
                  130

<210> SEQ ID NO 2
<211> LENGTH: 149
<212> TYPE: PRT
<213> ORGANISM: Mus Musculus

<400> SEQUENCE: 2

Met Lys Leu Pro Val Arg Leu Leu Val Leu Met Phe Trp Ile Pro Ala
             -15                 -10                  -5

Ser Ser Asp Asp Val Leu Met Thr Gln Thr Pro Leu Ser Leu Pro Val
         -1   1               5                  10

Ser Leu Gly Asp Gln Ala Ser Ile Ser Cys Arg Ser Gln Ser Ile
             15                  20                  25

Val His Ser Asn Gly Asn Thr Tyr Leu Glu Trp Tyr Leu Gln Lys Pro
 30                  35                  40                  45

Gly Gln Ser Pro Asn Leu Leu Ile Tyr Phe Val Ser Asn Arg Phe Ser
                 50                  55                  60

Gly Val Pro Asp Arg Phe Ser Gly Ser Gly Ser Gly Thr Asp Phe Thr
             65                  70                  75

Leu Lys Ile Ser Arg Val Glu Ala Glu Asp Leu Gly Val Tyr Tyr Cys
         80                  85                  90

Phe Gln Gly Ser His Val Pro Trp Thr Phe Gly Gly Gly Thr Lys Leu
     95                 100                 105

Glu Ile Lys Arg Ala Asp Ala Ala Pro Thr Val Ser Ile Phe Pro Pro
110                 115                 120                 125

Ser Ser Lys Leu Gly
                130

<210> SEQ ID NO 3
<211> LENGTH: 458
<212> TYPE: DNA
<213> ORGANISM: Mus Musculus
<220> FEATURE:
<221> NAME/KEY: CDS
<222> LOCATION: (1)..(456)
<221> NAME/KEY: mat_peptide
<222> LOCATION: (58)..(456)

<400> SEQUENCE: 3 atg gct gtc ttg ggg ctg ctc ttc tgc ctg gtg aca ttc cca agc tgt      48
Met Ala Val Leu Gly Leu Leu Phe Cys Leu Val Thr Phe Pro Ser Cys
             -15                 -10                  -5 gtc ctg tcc cag gtg cag gtg aag gag tca gga cct ttc ctg gtg ccc      96
Val Leu Ser Gln Val Gln Val Lys Glu Ser Gly Pro Phe Leu Val Pro
         -1   1               5                  10 ccc tca cag agc ctg tcc atc aca tgc act gtc tca ggg ttc tca tta     144
Pro Ser Gln Ser Leu Ser Ile Thr Cys Thr Val Ser Gly Phe Ser Leu
             15                  20                  25 acc acc tat ggt gta agc tgg att cgc cag cct cca gga aag ggt ctg     192
Thr Thr Tyr Gly Val Ser Trp Ile Arg Gln Pro Pro Gly Lys Gly Leu
 30                  35                  40                  45 gag tgg ctg gga gca att tgg ggt gac ggg acc aca aat tat cat tca     240
Glu Trp Leu Gly Ala Ile Trp Gly Asp Gly Thr Thr Asn Tyr His Ser
                 50                  55                  60 gct ctc ata tcc aga ctg agc atc agc aag gat aac tcc aag agc caa     288
Ala Leu Ile Ser Arg Leu Ser Ile Ser Lys Asp Asn Ser Lys Ser Gln
             65                  70                  75 gtt ttc tta aaa ctg aac agt ctg caa act gat gac acg gcc acg tac     336
Val Phe Leu Lys Leu Asn Ser Leu Gln Thr Asp Asp Thr Ala Thr Tyr
```

```
                            -continued
              80              85              90
tac tgt gcc aaa ctg ggt aac tac gat gct ctg gac tac tgg ggt caa    384
Tyr Cys Ala Lys Leu Gly Asn Tyr Asp Ala Leu Asp Tyr Trp Gly Gln
         95             100             105 gga acc tca gtc acc gtc tcc tca gcc aaa acg aca ccc cca ccc gtc    432
Gly Thr Ser Val Thr Val Ser Ser Ala Lys Thr Thr Pro Pro Pro Val
110             115             120             125 tat cca ttg gtc cct gga agc ttg gg                                 458
Tyr Pro Leu Val Pro Gly Ser Leu
             130

<210> SEQ ID NO 4
<211> LENGTH: 152
<212> TYPE: PRT
<213> ORGANISM: Mus Musculus

<400> SEQUENCE: 4

Met Ala Val Leu Gly Leu Leu Phe Cys Leu Val Thr Phe Pro Ser Cys
                -15             -10              -5

Val Leu Ser Gln Val Gln Val Lys Glu Ser Gly Pro Phe Leu Val Pro
         -1   1               5              10

Pro Ser Gln Ser Leu Ser Ile Thr Cys Thr Val Ser Gly Phe Ser Leu
        15              20              25

Thr Thr Tyr Gly Val Ser Trp Ile Arg Gln Pro Pro Gly Lys Gly Leu
 30              35              40                          45

Glu Trp Leu Gly Ala Ile Trp Gly Asp Gly Thr Thr Asn Tyr His Ser
                 50              55                  60

Ala Leu Ile Ser Arg Leu Ser Ile Ser Lys Asp Asn Ser Lys Ser Gln
                 65              70              75

Val Phe Leu Lys Leu Asn Ser Leu Gln Thr Asp Asp Thr Ala Thr Tyr
         80              85              90

Tyr Cys Ala Lys Leu Gly Asn Tyr Asp Ala Leu Asp Tyr Trp Gly Gln
         95             100             105

Gly Thr Ser Val Thr Val Ser Ser Ala Lys Thr Thr Pro Pro Pro Val
110             115             120             125

Tyr Pro Leu Val Pro Gly Ser Leu
             130

<210> SEQ ID NO 5
<211> LENGTH: 15
<212> TYPE: PRT
<213> ORGANISM: Artificial Sequence
<220> FEATURE:
<223> OTHER INFORMATION: Linking peptide

<400> SEQUENCE: 5

Gly Gly Gly Gly Ser Gly Gly Gly Gly Ser Gly Gly Gly Gly Ser
 1               5              10              15
```